United States Patent
Raes et al.

(10) Patent No.: US 11,649,508 B2
(45) Date of Patent: May 16, 2023

(54) INFLAMMATION ASSOCIATED, LOW CELL COUNT ENTEROTYPE

(71) Applicants: VIB VZW, Ghent (BE); KATHOLIEKE UNIVERSITEIT LEUVEN, K.U.LEUVEN R&D, Leuven (BE); VRIJE UNIVERSITEIT BRUSSEL, Brussels (BE)

(72) Inventors: Jeroen Raes, Berchem (BE); Gwen Falony, Nossegem (BE); Mireia Valles-Colomer, Leuven (BE); Lindsay Devolder, Brussels (BE); Severine Vermeire, Leuven (BE); Sara Vieira-Silva, Leuven (BE); João Guedelha Sabino, Leuven (BE); Marie D'Hooghe, Brussels (BE); Jacques De Keyser, Brussels (BE)

(73) Assignees: VIB VZW, Ghent (BE); KATHOLIEKE UNIVERSITES LEUVEN, K.U.LEUVEN R & D, Leuven (BE); VRIJE UNIVERSITES BRUSSEL, Brussels (BE)

( * ) Notice: Subject to any disclaimer, the term of this patent is extended or adjusted under 35 U.S.C. 154(b) by 243 days.

(21) Appl. No.: 16/771,856

(22) PCT Filed: Dec. 14, 2018

(86) PCT No.: PCT/EP2018/084920
§ 371 (c)(1),
(2) Date: Jun. 11, 2020

(87) PCT Pub. No.: WO2019/115755
PCT Pub. Date: Jun. 20, 2019

(65) Prior Publication Data
US 2021/0172006 A1    Jun. 10, 2021

(30) Foreign Application Priority Data

Dec. 15, 2017 (EP) .................................. 17207770
May 30, 2018 (EP) .................................. 18175094

(51) Int. Cl.
*C12Q 1/689* (2018.01)

(52) U.S. Cl.
CPC ........ *C12Q 1/689* (2013.01); *C12Q 2600/112* (2013.01)

(58) Field of Classification Search
CPC .......................... C12Q 1/689; C12Q 2600/112
USPC ....................................................... 424/145.1
See application file for complete search history.

(56) References Cited

FOREIGN PATENT DOCUMENTS

WO    2017025617 A1    2/2017

OTHER PUBLICATIONS

Schwiertz et al. Microbiota in Pediatric Inflammatory Bowel Disease. J Pediatr2010;157:240-244. (Year: 2010).*
Vandeputte et al. Quantitative microbiome profiling links gut community variation to microbial load. Nature vol. 551, p. 507-511, Published online: Nov. 15, 2017 (21 pages) (Year: 2017).*
Caenepeel, C., et al. "Quantitative Microbiome Profiling Changes the Described Dysbiotic State in Inflammatory Bowel Disease." Journal of Crohns Colitis, vol. 12, No. s1, 2018, pp. S548-S549.
Costello, Mary-Ellen, et al. "Brief Report: Intestinal Dysbiosis in Ankylosing Spondylitis: Gut Microbiome and AS-Related Genes." Arthritis Rheumatology, vol. 67, No. 3, 2015, pp. 686-691.
Natividad, Jane M., et al. "Antimicrobial-Induced Dysbiosis Excerbates Colitis in NOD1(-/-);NOD2(-/-) Mice." Gastroenterology, vol. 142, No. 5, 2012, p. S196.
PCT International Search Report and Written Opinion; Application No. PCT/EP2018/084920, International filing date of Dec. 14, 2018, VIB VZW, Authorized Officer Nuria Costa Roldan, dated Feb. 25, 2019, 10 pages.
Sokol, et al. "Low Counts of Faecalibacterium Prausnitzii in Colitis Microbiota." Inflammatory Bowel Diseases, vol. 15, No. 8, 2009, pp. 1183-1189.
Vandeputte, Doris et al., "Quantitative Microbiome Profiling links Gut Community Variation to Microbial Load" Nature, Nov. 23, 2017, London, vol. 551, pp. 507-511.

* cited by examiner

Primary Examiner — Yih-Horng Shiao
(74) Attorney, Agent, or Firm — Patent Law Works, LLP

(57) ABSTRACT

The present invention relates to the field of inflammation-associated disorders or conditions, more particularly to gut inflammation. Provided herein are means and methods to diagnose and treat or reduce the severity of inflammation-associated disorders or conditions in a subject in need thereof.

6 Claims, 7 Drawing Sheets
(7 of 7 Drawing Sheet(s) Filed in Color)

INFLAMMATION ASSOCIATED, LOW CELL COUNT ENTEROTYPE

CROSS REFERENCE TO RELATED APPLICATIONS

This application is a national phase entry under 35 U.S.C. § 371 of International Patent Application PCT/EP2018/0684920, filed Dec. 14, 2018, designating the United States of America and published in English as International Patent Publication WO 2019/115755 A1 on Jun. 20, 2019, which claims the benefit under Article 8 of the Patent Cooperation Treaty to European Patent Application Serial No. 17207770.3, filed Dec. 15, 2017, and European Patent Application Serial No. 18175094.4, filed May 30, 2018, the entireties of each of which are hereby incorporated by reference.

FIELD OF THE INVENTION

The present invention relates to the field of inflammation-associated disorders or conditions, more particularly to gut inflammation and inflammation associated with primary sclerosing cholangitis, spondyloarthritis or multiple sclerosis. Provided herein are means and methods to diagnose and treat or reduce the severity of inflammation-associated disorders or conditions in a subject in need thereof.

BACKGROUND

The human body is home to several microbes including bacteria, archaea, viruses and fungi. Different microbial communities thrive in the different body habitats (e.g. mouth, nose, gut, skin, vagina). The richness and complexity of these microbial communities varies according to the body habitats, being higher in the sites linked to the gastrointestinal tract. These communities are relatively stable over time in a healthy individual, in contrast with inter-individual variation which is high among healthy individuals (The Human Microbiome Project Consortium 2012 Nature 486: 207-214). The gut is by far the richest microbial habitat in the human body. These intestinal symbionts co-exist with the host in a mutualistic, commensal or parasitic relationship. Many important metabolic, immunological, and trophic functions have been attributed to the interaction between the gut microbiota and the host. Interindividual differences in the gut microbiota composition are usually derived from variations in the core-microbiota, which are microbes that are roughly ubiquitous in the population. Three core-microbiota genera (*Bacteroides, Ruminococcus* and *Prevotella*) are the drivers of the identified human enterotypes, which are genera-driven clusters based on the overall microbiota composition (Arumugam et al 2011 Nature 473:174-180; Falony et al 2016 Science 352:560-564). The majority of bacteria living in the gut is not identified by methods depending on culturing of bacteria. Therefore, the development of culturing-independent methods (e.g. denaturing gradient gel electrophoresis, 16S rRNA gene sequencing, shotgun sequencing) for identifying these organisms has greatly expanded the knowledge of the intestinal microbiota. However, most of these methods only provide the relative composition of the microbiota, and quantification of complex microbial ecosystems has still to be widely implemented. Consequently, the analysis of the intestinal microbiota has been focused to microbiota diversity (how many different organisms are present in one sample) and composition (microbiota profile based on the number and relative amount of organisms present in one sample). Recently, using quantitative microbiome profiling (QMP) the Bacteroides enterotype could be differentiated into two clusters, i.e. Bacteroides1 (B1) and Bacteroides2 (B2) based on cell densities (Vandeputte et al 2017 Nature doi:10.1038/nature24460).

Perturbation of the gut microbiota, or dysbiosis, has been the subject of extensive research in several diseases such as asthma (Fujimura et al 2016 Nat Med 22:1187-1191), obesity (Turnbaugh et al 2009 Nature 457:480-484) and inflammatory bowel diseases (IBD) (Machiels et al 2014 Gut 63:1275-1283; Joossens et al 2011 Gut 60:631-637). Inflammatory bowel disease (IBD) is an umbrella term referring to certain chronic diseases that cause inflammation of the intestines, among which Crohn's disease (CD) and ulcerative colitis (UC). Patients with IBD suffer from a panoply of symptoms including diarrhea, abdominal pain, loss of weight, fever, fatigue, malaise and anorexia. In children, growth failure can also be observed. Being a systemic disease, IBD is also associated with extra-intestinal manifestations. Between 6-47% of the patients with IBD suffer at least from one extra-intestinal manifestation, being dermatological (e.g. pyoderma gangrenosum, erythema nodosum), ophthalmological (e.g. uveitis, conjunctivitis), rheumatological (e.g. spondyloartropathy, arthralgia) or hepatic disorders (e.g. primary sclerosing cholangitis—PSC) (Ott and Scholmerich 2013 Nat Rev Gastroenterol Hepatol 10:585-595). Clinical suspicion of IBD requires initial blood testing and exclusion of infectious cause. Thereafter, the mainstay to confirm the diagnosis of IBD is by endoscopic evaluation complemented by histologic evidence of IBD (Dignass et al 2012 J Crohns Colitis 6:965-990). Additional radiographic evaluation can sometimes be helpful in the diagnosis of IBD to detect upper or more complicated disease involving strictures and fistulae (Van Assche et al 2010 J Crohns Colitis 4:7-27). During the follow-up, disease activity can be evaluated through a combination of symptom evaluation, biomarkers, endoscopic evaluation and radiographic imaging. C-reactive protein (CRP) is a serum marker of systemic inflammation with lower sensitivity for intestinal inflammation. Recently, fecal calprotectin, a fecal marker for intestinal inflammation, became widely available. In patients with UC and colonic CD, low fecal calprotectin correlates with endoscopic and histologic remission (Zittan et al 2016 Inflamm Bowel Dis 22:623-630). Furthermore, an increase of fecal calprotectin in consecutive timepoints is predictive for disease relapse in patients with UC (De Vos et al 2013 Inflamm Bowel Dis 19:2111-2117). Therefore, it would be advantageous to develop simple, fast, non-invasive and reliable detection methods for IBD and for inflammation associated diseases such as primary sclerosing cholangitis, multiple sclerosis and spondyloarthritis.

We recently devised a method for quantitative microbiota profiling (QMP) by combining microbial load assessments by flow cytometry and metagenomics (Vandeputte et al 2017 Nature). This pioneering study showed that human stool samples differ considerably in microbial load even in healthy individuals and that associations with relative microbiota profiles (RMP) can be misleading. In this application we analysed a primary sclerosing cholangitis (PSC), IBD and multiple sclerosis (MS) cohort with quantitative microbiota profiling to refine the study of dysbiosis in these complex disorders. Perturbation of the gut microbiota, or dysbiosis, has been the subject of extensive research in Crohn's disease (CD) and ulcerative colitis (UC), the two main phenotypes of IBD (Sartor et al 2017 Gastroenterology 152:327-339). In CD, a decrease of bacterial diversity,

*Faecalibacterium prausnitzii, Bifidobacterium adolescentis* and *Roseburia intestinalis* parallels an increase in *Escherichia coli*, and the genera *Veillonella* and *Fusobacterium* (Joossens et al 2011 Gut 60:631-637; Gevers et al 2014 Cell Host Microbe 15:382-392; Darfeuille-Michaud et al 2004 Gastroenterology 127:412-421; Sokol et al 2008 Proc Natl Acad Sci USA 105:16731-16736; Willing et al 2010 Gastroenterology 139:1844-1854; Mottawea et al 2016 Nat Commun 7:13419). A decrease in *Faecalibacterium prausnitzii* and *Roseburia hominis* is associated with UC (Machiels et al 2014 Gut 63:1275-1283; Vermeiren et al 2012 FEMS Microbiol Ecol 79:685-696; Wang et al 2014 J Clin Microbiol 52:398-406). More recently, PSC-associated dysbiosis was also characterized (Sabino et al 2016 Gut 65:1681-1689), but all these studies were performed with relative microbiota profiling.

Given that all analyses so far were performed using relative microbiome profiling, cell counts of bacterial strains were not taken into account. Using QMP, we found a clear association between the recently defined *Bacteroides* 2 enterotype and IBD, PSC and MS types which are linked with inflammation and therefore disclose that the low cell count B2 enterotype is a general inflammation-associated enterotype.

SUMMARY

Stool samples from patients with multiple sclerosis (MS), primary sclerosing cholangitis (PSC) and/or inflammatory bowel disease were analysed in the background of the Flemish Gut Flora Project. 16S rRNA gene sequencing was performed with Illumina MiSeq technology. Flow cytometry was used to count the bacterial load of each sample. Relative and quantitative microbiota profiling (QMP) were compared in this cohort. We observed a positive correlation between bacterial load and inflammatory markers, fecal calprotectin and CRP. The presence of inflammation influenced the intestinal microbiota composition. Additionally, the *Bacteroides*2 enterotype was found to be predominantly present in patients, being underrepresented in healthy individuals. The *Bacteroides*2 enterotype is also associated with systemic and intestinal inflammation, lower microbial diversity and lower microbial richness, suggesting that the *Bacteroides*2 enterotype may depict a vulnerable microbial community associated with disease or pre-disease status. Moreover, *Faecalibacterium* was negatively correlated with increased fecal calprotectin, while the genera *Fusobacterium, Veillonella, Escherichia, Shigella* and *Streptococcus* increased with increasing fecal calprotectin. However, in stool samples from the PSC/IBC cohort we observed a striking co-exclusion between *Fusobacterium* and *Veillonella*. Intestinal inflammation is associated with reduced fecal cell counts. We disclose here that the *Bacteroides*2 enterotype represents a disease-prone intestinal microbiota composition. Therapeutic strategies that increase microbial load and microbial resilience may prevent development of intestinal inflammation.

Therefore, it is an object of the invention to provide a method of detecting an inflammatory disorder in a subject, said method comprising detecting whether a stool sample of said subject has a lower microbial cell count compared to a stool sample of a healthy subject and a high relative fraction of the Bacteroides genus within said stool sample of said subject to be diagnosed. It is also an object of the invention to provide a method of diagnosing and treating an inflammatory disorder in a subject wherein said method comprises the steps of:

Quantifying the number of bacterial cells in a stool sample of said subject;

Determining the microbiome composition of said stool sample;

Diagnosing said subject with an inflammatory disorder when said stool sample is characterized by lower cell count compared to a stool sample of a healthy subject and a high relative fraction of the *Bacteroides* genus within said stool sample of said subject to be diagnosed and treated;

Administering an effective amount of anti-inflammatory medication to the diagnosed subject.

In particular embodiments of the above methods, the detection of the relative fraction of the *Bacteroides* genus can be replaced or supplemented by the detection of the relative fraction of the *Faecalibacterium* genus, wherein a low relative fraction of the *Faecalibacterium* genus within the stool sample of the subject to be diagnosed together with a microbial cell count of said sample that is lower than the microbial cell count of a stool sample of a healthy subject (and optionally by a low relative fraction of the *Bacteroides* genus within the stool sample of the subject to be diagnosed) is indicative for said subject to have or to develop an inflammatory disorder. In particular embodiments, the *Bacteroides* and/or *Faecalibacterium* genus is determined using microbiota phylogenetic profiling, wherein said phylogenetic profiling is performed using PCR, RT-PCR, qPCR, multiplex PCR, high-throughput sequencing, metatranscriptomic sequencing, identification of strain-specific markers and/or 16S rRNA analysis. In other particular embodiments, said stool sample of said subject used to diagnose said subject with an inflammatory disease is further characterized by a lower bacterial diversity compared to a stool sample of a healthy subject.

In particular embodiments, the inflammatory disorders for which said application provides diagnostic methods are gut inflammatory disorders or inflammatory associated with primary sclerosing cholangitis, multiple sclerosis or spondyloarthritis. Even more particularly, said gut inflammatory disorder is selected from the list consisting of Crohn's disease, irritable bowel syndrome, inflammatory bowel disease (IBD), ulcerative colitis, celiac disease, and gut inflammation associated with primary sclerosing cholangitis, multiple sclerosis or spondyloarthritis.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
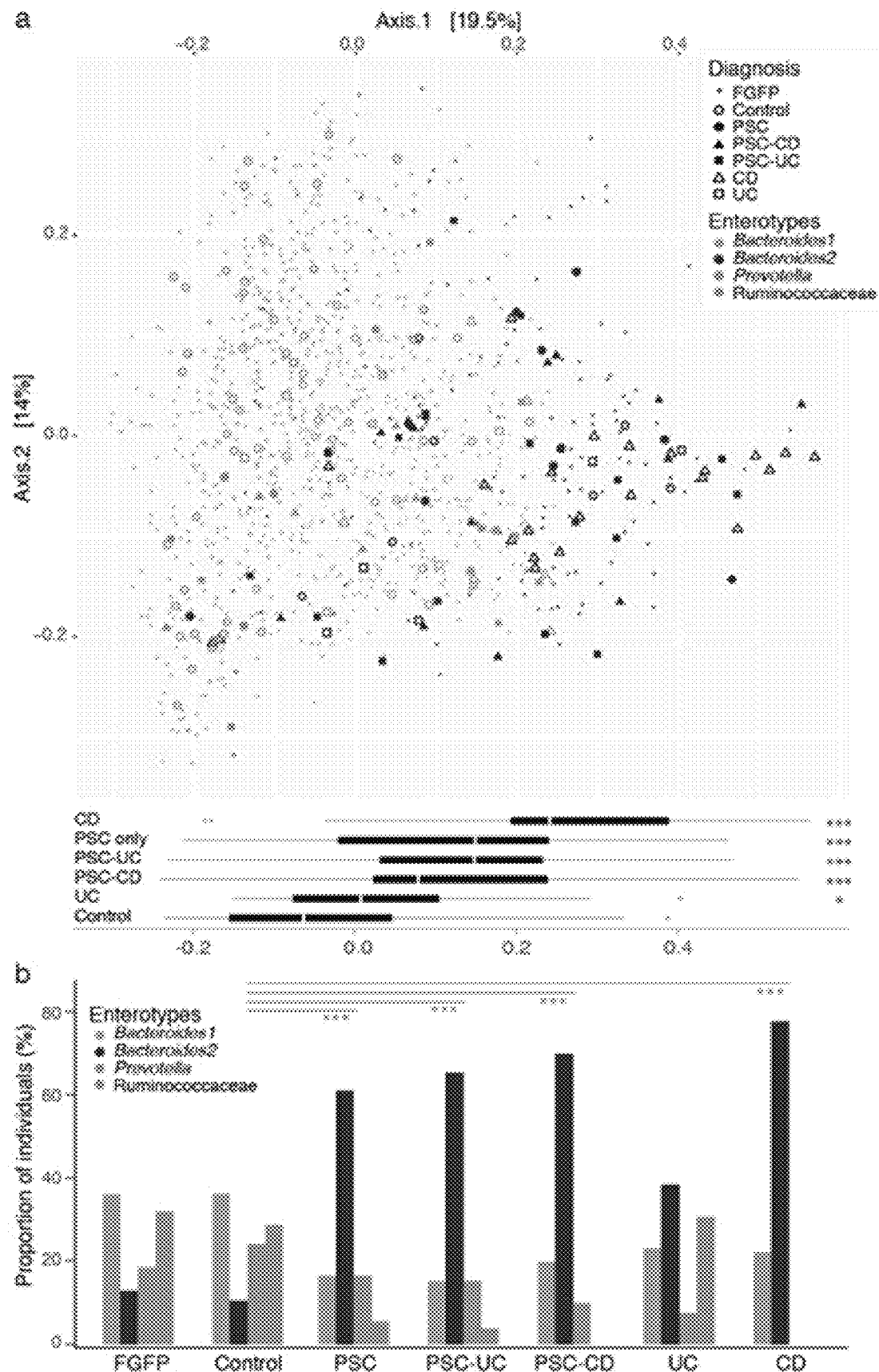
FIG. 1. Microbial composition of the PSC and IBD cohort. (a) Principal coordinates analysis of inter-individual differences (Bray-Curtis) in relative microbiome profiles of the PSC/IBD cohort (N=104) using a cross-section of the Flemish population as background (FGFP, N=1120 including 66 PSC/PSC-CD matched controls). The distribution of samples along the first axis of the PCoA (lower panel boxplots) separates healthy controls and the different patient groups: IBD (UC, CD), PSC without IBD (PSC) and PSC with concomitant IBD (PSC-UC, PSC-CD). Kruskal-Wallis with post-hoc Dunn test, patient groups versus controls: FDR<0.001(*); <0.01(); <0.05(*). (b) Prevalence of each enterotype in the control and patient groups. $Chi^2$ test FDR <0.001(*), <0.01(). Bars represent from left to right: *Bacteroides* 1 (green); *Bacteroides* 2 (black); *Prevotella* (purple) and *Ruminococcaceae* (orange).

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Michael R. Green and Joseph Sambrook, Molecular Cloning: A Laboratory Manual, 4$^{th}$ ed., Cold Spring Harbor Laboratory Press, Plainsview, N.Y. (2012); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

Standard amplicon sequencing and metagenomic analyses of the fecal microbiota quantify microbial taxa and metabolic pathways as fractions of the sample sequence library generated (Zhernakova et al 2016 Science 352: 565-569; Falony et al 2016 Science 352: 560-564). While such relative approaches do allow detection of disease-associated microbiome variation and identification of associated markers, they are limited in their ability to dissect the interplay between microbiota and host health (Valles-Colomer et al 2016 J Crohns Colitis 10:735-746; Satinsky et al 2013 Methods Enzymol 531: 237-250). Comparative analyses of relative microbiome data cannot provide information on the extent or directionality of changes in taxa abundances or metabolic potential (Morton et al 2017 mSystems 2, e00162-16). In case of substantial variation of microbial load between samples, relative profiling will hamper linking microbiome features to quantitative data such as physiological parameters or metabolite concentrations (Morton et al 2017 mSystems 2, e00162-16; Gloor et al 2016 Ann Epidemiol 26:322-329). Above all, relative approaches ignore the hypothesis that reduced overall microbiota abundance per se could be a key identifier of a disease-associated ecosystem configuration (Harmsen et al 2012 Clin vaccine Immunol 19: 515-521). Hence, in order to enable genuine characterization of host-microbiota interactions, microbiome research must trade in ratios for counts. In this application, the inventors used a recently developed quantitative microbiome profiling (QMP) method to study gut microbiota variation in patients with different forms of inflammatory disorders. The QMP method is a combination of microbiome profiling and flow cytometric enumeration of microbial cells, addressing the challenges inherent to the quantitative analysis of a highly dense and complex microbiota embedded in a semi-solid matrix (Vandeputte et al 2017 Nature).

In a first aspect, a method of detecting an inflammatory disorder in a subject is provided, said method comprising detecting whether a stool sample of said subject has a low microbial cell count and has a high relative fraction of the *Bacteroides* genus and/or a low relative fraction of the *Faecalibacterium* genus.

Also a method of diagnosing an inflammatory disorder in a patient is provided, said method comprising determining whether a stool sample of said patient has a low microbial cell count and has a high relative fraction of the *Bacteroides* genus and/or a low relative fraction of the *Faecalibacterium* genus.

Also a method for measuring the probability of a subject developing or having an inflammatory disorder is provided, said method comprising measuring the microbial cell count of a stool sample of said subject, measuring the abundance of at least 10, at least 50 or at least 100 bacterial genera comprising the *Bacteroides* genus in said stool sample and determining the probability of the subject developing or having an inflammatory disorder, wherein a low microbial cell count and a high relative abundance of the *Bacteroides* genus in said stool sample indicates a high probability of the subject developing an inflammatory disorder. Particularly, said high relative abundance of the *Bacteroides* genus means that the *Bacteroides* genus belongs to the 25%, 10%, 5%, 3%, 2% or 1% most abundant genera in said stool sample of said subject. In another embodiment, a method is provided for measuring the probability of a subject developing or having an inflammatory disorder, said method comprising measuring the microbial cell count of a stool sample of said subject, measuring the abundance of at least 10, at least 50 or at least 100 bacterial genera comprising the *Faecalibacterium* genus in said stool sample and determining the probability of the subject developing or having an inflammatory disorder, wherein a low microbial cell count and a low relative abundance of the *Faecalibacterium* genus in said stool sample indicates a high probability of the subject developing an inflammatory disorder. Particularly, said low relative abundance of the *Faecalibacterium* genus means that the *Faecalibacterium* genus belongs to the 25%, 10%, 5%, 3%, 2% or 1% least abundant genera in said stool sample of said subject. In yet another embodiment, a method is provided for measuring the probability of a subject developing or having an inflammatory disorder, said method comprising measuring the microbial cell count of a stool sample of said subject, measuring the abundance of at least 10, at least 50 or at least 100 bacterial genera comprising the *Bacteroides* and *Faecalibacterium* genera in said stool sample and determining the probability of the subject developing or having an inflammatory disorder, wherein a low microbial cell count and a high relative abundance of the *Bacteroides* genus together with a low relative abundance of the *Faecalibacterium* genus in said stool sample indicates a high probability of the subject developing an inflammatory disorder. In a most particular embodiment, said high relative abundance of the *Bacteroides* genus means that the *Bacteroides* genus belongs to the 10% most abundant genera in said stool sample of said subject and said low relative abundance of the *Faecalibacterium* genus means that the *Faecalibacterium* genus belongs to the 10% least abundant genera in said stool sample of said subject and said low microbial cell count is less than $1.5 \times 10^{11}$ cell per gram of fresh stool.

In order to diagnose a subject with an inflammatory disorder or to detect an inflammatory disorder with a subject, the microbial cell count of a fecal or stool sample should be determined and the relative fraction or relative abundance of the *Bacteroides* genus and/or *Faecalibacterium* genus should be determined in view of a plurality of detectable and/or measurable bacterial genera analyzed or present in the stool sample. Therefore, in one embodiment, a method of detecting an inflammatory disorder in a subject is provided, said method comprising the steps of quantifying or measuring the number of bacterial cells in a stool or fecal sample of said subject, determining the microbiome composition of said stool sample and detecting or measuring whether said stool sample is characterized by low cell count and by a high relative fraction of the *Bacteroides* genus and/or a lower relative fraction of the *Faecalibacterium* genus. The order or sequence of the cell count measurements and the gut microbiome composition analysis is not important and will not influence the outcome of the diagnosis. Hence, in another embodiment, a method of detecting an inflammatory disorder in a subject is provided, said method comprising the steps of determining the microbiome composition or microbiome profile of a stool or fecal sample of said subject, quantifying the number of bacterial cells in said stool sample, and detecting whether said stool sample is characterized by a low cell count and by a high relative fraction of the *Bacteroides* genus and/or a low relative fraction of the *Faecalibacterium* genus.

In particular embodiments of all the aspects and their embodiments disclosed in this application, said "low microbial cell count" is a cell count of less than $2 \times 10^{11}$, less than $1.5 \times 10^{11}$, less than $1 \times 10^{11}$, less than $9 \times 10^{10}$, less than $8 \times 10^{10}$, less than $7 \times 10^{10}$, less than $6 \times 10^{10}$, less than $5 \times 10^{10}$, less than $4 \times 10^{10}$, less than $3 \times 10^{10}$, less than $2 \times 10^{10}$, less than $1.5 \times 10^{10}$, less than $1 \times 10^{10}$, less than $9 \times 10^{9}$, less than $8 \times 10^{9}$, less than $7 \times 10^{9}$, less than $6 \times 10^{9}$, less than $5 \times 10^{9}$, less than $4 \times 10^{9}$, less than $3 \times 10^{9}$, less than $2 \times 10^{9}$, less than $1.5 \times 10^{9}$, less than $1 \times 10^{9}$, less than $5 \times 10^{8}$ or less than $5 \times 10^{8}$ cells per gram stool. More particularly, low microbial cell count is a cell count of less than $1.5 \times 10^{11}$ cells per gram stool.

In particular embodiments of all the aspects and their embodiments disclosed in this application, said "high relative fraction of the *Bacteroides* genus" means that the *Bacteroides* genus belongs to the most abundant genera in said stool sample of said subject. More particularly, said most abundant genera are the 100, 50, 40, 30, 20, 10, 9, 8, 7, 6, 5, 4, 3 or 2 most abundant genera in said stool sample of said subject. Even more particularly, said most abundant genera are the 25%, 10%, 5%, 3%, 2% or 1% most abundant genera in said stool sample of said subject. In most particular embodiments of all the methods disclosed in this application, said "high relative fraction of the *Bacteroides* genus" means that the *Bacteroides* genus is the most abundant genus in said stool sample of said subject.

In other embodiments, said "high relative fraction of the *Bacteroides* genus" is an abundance of the *Bacteroides* genus which is at least 10%, at least 20%, at least 30%, at least 40%, at least 50%, at least 60%, at least 70%, at least 80%, at least 90%, at least 100%, at least 1.5 fold, at least 2 fold, at least 3 fold, at least 5 fold or at least 10 fold higher than the abundance of the other measured or detected bacterial genera in the stool sample of said subject. Said abundance can be the average abundance of the other measured bacterial genera in said stool sample.

In particular embodiments of all the aspects and their embodiments disclosed in this application, said "low relative fraction of the *Faecalibacterium* genus" means that the *Faecalibacterium* genus belongs to the least abundant genera in said stool sample of said subject. More particularly, said least abundant genera are the 100, 50, 40, 30, 20, 10, 9, 8, 7, 6, 5, 4, 3 or 2 least abundant genera in said stool sample of said subject. Even more particularly, said least abundant genera are the 25%, 10%, 5%, 3%, 2% or 1% least abundant genera in said stool sample of said subject. In most particular embodiments of all the methods disclosed in this application, said "low relative fraction of the *Faecalibacterium* genus" means that the *Faecalibacterium* genus is the least abundant genus in said stool sample of said subject.

In other embodiments, said "low relative fraction of the *Faecalibacterium* genus" is an abundance of the *Faecalibacterium* genus which is at least 10%, at least 20%, at least 30%, at least 40%, at least 50%, at least 60%, at least 70%, at least 80%, at least 90%, at least 100%, at least 1.5 fold, at least 2 fold, at least 3 fold, at least 5 fold or at least 10 fold lower than the abundance of the other measured or detected bacterial genera in the stool sample of said subject. Said abundance can be the average abundance of the other measured bacterial genera in said stool sample.

In most particular embodiments, said "low microbial cell count" is a cell count of less than $1.5 \times 10^{11}$ cells per gram stool, said "high relative fraction of the *Bacteroides* genus" means that the *Bacteroides* genus belongs to the 10% most abundant genera in said stool sample of said subject and said "low relative fraction of the *Faecalibacterium* genus" means that the *Faecalibacterium* genus belongs to the 25% least abundant genera in said stool sample of said subject. In most particular embodiments, said "low microbial cell count" is a cell count of less than $1.5 \times 10^{11}$ cells per gram stool, said "high relative fraction of the *Bacteroides* genus" means that the *Bacteroides* genus belongs to the 5% most abundant genera in said stool sample of said subject and said "low relative fraction of the *Faecalibacterium* genus" means that the *Faecalibacterium* genus belongs to the 25% least abundant genera in said stool sample of said subject. In most particular embodiments, said "low microbial cell count" is a cell count of less than $1.5 \times 10^{11}$ cells per gram stool, said "high relative fraction of the *Bacteroides* genus" means that the *Bacteroides* genus belongs to the 10% most abundant genera in said stool sample of said subject and said "low relative fraction of the *Faecalibacterium* genus" means that the *Faecalibacterium* genus belongs to the 5% least abundant genera in said stool sample of said subject. In most particular embodiments, said "low microbial cell count" is a cell count of less than $1.5 \times 10^{11}$ cells per gram stool, said "high relative fraction of the *Bacteroides* genus" means that the *Bacteroides* genus belongs to the 25% most abundant genera in said stool sample of said subject and said "low relative fraction of the *Faecalibacterium* genus" means that the *Faecalibacterium* genus belongs to the 10% least abundant genera in said stool sample of said subject. In most particular embodiments, said "low microbial cell count" is a cell count of less than $1.5 \times 10^{11}$ cells per gram stool, said "high relative fraction of the *Bacteroides* genus" means that the *Bacteroides* genus belongs to the 25% most abundant genera in said stool sample of said subject and said "low relative fraction of the *Faecalibacterium* genus" means that the *Faecalibacterium* genus belongs to the 5% least abundant genera in said stool sample of said subject. In most particular embodiments, said "low microbial cell count" is a cell count of less than $1.5 \times 10^{11}$ cells per gram stool, said "high relative fraction of the *Bacteroides* genus" means that the *Bacteroides* genus belongs to the 3% most abundant genera in said stool sample of said subject and said "low relative fraction of the *Faecalibacterium* genus" means that the *Faecalibacterium* genus belongs to the 3% least abundant genera in said stool sample of said subject. In most particular embodiments, said "low microbial cell count" is a cell count of less than $1.5 \times 10^{11}$ cells per gram stool, said "high relative fraction of the *Bacteroides* genus" means that the *Bacteroides* genus belongs to the 1% most abundant genera in said stool sample of said subject and said "low relative fraction of the *Faecalibacterium* genus" means that the *Faecalibacterium* genus belongs to the 1% least abundant genera in said stool sample of said subject.

The methods herein described can also be successfully used to diagnose a subject with one of the inflammatory disorders mentioned herein when the stool sample of the subject to be diagnosed is compared to a stool sample of a healthy person. Therefore, methods of detecting an inflammatory disorder in a subject are provided, said method comprising detecting whether a stool sample of said subject has a low microbial cell count and has a high relative fraction of the *Bacteroides* genus and/or a low relative fraction of the *Faecalibacterium* genus, wherein the microbial cell count and the abundance of the *Bacteroides* and/or *Faecalibacterium* genus are compared to a stool sample of a healthy subject. In particular embodiments, said "low microbial cell count" is a microbial cell count which is at least 10%, at least 20%, at least 30%, at least 40%, at least 50%, at least 60%, at least 70%, at least 80%, at least 90%, at least 100%, at least 1.5 fold, at least 2 fold, at least 3 fold, at least 5 fold or at least 10 fold lower than the microbial count of a stool sample of a healthy subject. In other embodiments, said "high relative fraction of the *Bacteroides* genus" is an at least 10%, at least 20%, at least 30%, at least 40%, at least 50%, at least 60%, at least 70%, at least 80%, at least 90%, at least 100%, at least 1.5 fold, at least 2 fold, at least 3 fold, at least 5 fold or at least 10 fold higher relative abundance compared to the relative abundance of the *Bacteroides* genus in the stool sample of a healthy subject. In other particular embodiments, said "low relative fraction of the *Faecalibacterium* genus" is an at least 10%, at least 20%, at least 30%, at least 40%, at least 50%, at least 60%, at least 70%, at least 80%, at least 90%, at least 100%, at least 1.5 fold, at least 2 fold, at least 3 fold, at least 5 fold or at least 10 fold lower relative abundance compared to the relative abundance of the *Faecalibacterium* genus in the stool sample of a healthy subject.

In particular embodiments, said low microbial cell count of a stool sample of a patient diagnosed with an inflammatory disorder is between 2 and 5 fold lower than that of a healthy subject and the high relative abundance of the *Bacteroides* genus between 1.5 and 3 fold higher than that of a healthy subject and/or the low relative abundance of the *Faecalibacterium* genus between 1.5 and 3 fold lower than that of a healthy subject. In other particular embodiments, said low microbial cell count of a stool sample of a patient diagnosed with an inflammatory disorder is between 3 and 8 fold lower than that of a healthy subject and the high relative abundance of the *Bacteroides* genus between 1.5 and 3 fold higher than that of a healthy subject and/or the low relative abundance of the *Faecalibacterium* genus between 1.5 and 3 fold lower than that of a healthy subject. In other particular embodiments, said low microbial cell count of a stool sample of a patient diagnosed with an inflammatory disorder is between 1.5 and 6 fold lower than that of a healthy subject and the high relative abundance of the *Bacteroides* genus between 1.5 and 3 fold higher than that of a healthy subject and/or the low relative abundance of the *Faecalibacterium* genus between 2 and 5 fold lower than that of a healthy subject. In other particular embodiments, said low microbial cell count of a stool sample of a patient diagnosed with an inflammatory disorder is between 1.5 and 6 fold lower than that of a healthy subject and the high relative abundance of the *Bacteroides* genus between 2 and 5 fold higher than that of a healthy subject and/or the low relative abundance of the *Faecalibacterium* genus between 1.5 and 3 fold lower than that of a healthy subject. In other particular embodiments, said low microbial cell count of a stool sample of a patient diagnosed with an inflammatory disorder is between 1.5 and 6 fold lower than that of a healthy subject and the high relative abundance of the *Bacteroides* genus between 2 and 5 fold higher than that of a healthy subject and/or the low relative abundance of the *Faecalibacterium* genus between 2 and 5 fold lower than that of a healthy subject. In other particular embodiments, said low microbial cell count of a stool sample of a patient diagnosed with an inflammatory disorder is between 2 and 5 fold lower than that of a healthy subject and the high relative abundance of the *Bacteroides* genus between 25% and 75% higher than that of a healthy subject and/or the low relative abundance of the *Faecalibacterium* genus between 2 and 5 fold lower than that of a healthy subject. In other particular embodiments, said low microbial cell count of a stool sample of a patient diagnosed with an inflammatory disorder is between 2 and 5 fold lower than that of a healthy subject and the high relative abundance of the *Bacteroides* genus between 50% and 2 fold higher than that of a healthy subject and/or the low relative abundance of the *Faecalibacterium* genus between 2 and 5 fold lower than that of a healthy subject. In other particular embodiments, said low microbial cell count of a stool sample of a patient diagnosed with an inflammatory disorder is between 2 and 5 fold lower than that of a healthy subject and the high relative abundance of the *Bacteroides* genus between 25% and 75% higher than that of a healthy subject and/or the low relative abundance of the *Faecalibacterium* genus between 25% and 75% fold lower than that of a healthy subject. In other particular embodiments, said low microbial cell count of a stool sample of a patient diagnosed with an inflammatory disorder is between 2 and 5 fold lower than that of a healthy subject and the high relative abundance of the *Bacteroides* genus between 50% and 2 fold higher than that of a healthy subject and/or the low relative abundance of the *Faecalibacterium* genus between 25% and 75% fold lower than that of a healthy subject. In other particular embodiments, said low microbial cell count of a stool sample of a patient diagnosed with an inflammatory disorder is between 2 and 5 fold lower than that of a healthy subject and the high relative abundance of the *Bacteroides* genus between 25% and 75% higher than that of a healthy subject and/or the low relative abundance of the *Faecalibacterium* genus between 50% and 2 fold lower than that of a healthy subject. In other particular embodiments, said low microbial cell count of a stool sample of a patient diagnosed with an inflammatory disorder is between 2 and 5 fold lower than that of a healthy subject and the high relative abundance of the *Bacteroides* genus between 2 and 5 fold higher than that of a healthy subject and/or the low relative abundance of the *Faecalibacterium* genus between 25% and 75% fold lower than that of a healthy subject. In other particular embodiments, said low microbial cell count of a stool sample of a patient diagnosed with an inflammatory disorder is between 2 and 5 fold lower than that of a healthy subject and the high relative abundance of the *Bacteroides* genus between 2 and 5 fold higher than that of a healthy subject and/or the low relative abundance of the *Faecalibacterium* genus between 50% and 2 fold lower than that of a healthy subject.

In particular embodiments, "method to detect an inflammatory disorder" is equivalent to a "method to detect the presence or to assess the risk of development of an inflammatory disease".

"Stool sample" and "fecal sample" are used interchangeably and refer to as a sample or aliquot of the stool or feces of a subject, more particular a mammal, even more particularly a human being, most particularly a patient. The stool sample as used herein comprises the gut microbiome from a human patient to be diagnosed. As used herein, the term "microflora" refers to the collective bacteria in an ecosystem of a host (e.g. an animal, such as a human) or in a single part of the host's body, e.g. the gut. An equivalent term is "microbiota". As used herein, the term "microbiome" refers to the totality of bacteria, their genetic elements (genomes) in a defined environment, e.g. within the gut of a host, the latter then being referred to as the "gut microbiome".

"Cell count" as used herein refers to the sample cell density, in order words how many cells, more particularly microbial cells, are present in the sample, more particularly stool sample. Multiple methods are known by the skilled person to quantify microbial cell count in a stool sample, which is typically presented as cells per gram stool.

"Relative fraction" or "relative abundance" as used herein refers to the fraction or abundance of a certain genus with respect to or compared to a plurality of other genera present in the stool sample.

"*Bacteroides*" as used herein refers to a genus of Gram-negative, obligate anaerobic bacteria. *Bacteroides* species are normally mutualistic, making up the most substantial portion of the mammalian gastrointestinal flora. The *Bacteroides* genus belongs to the family of Bacteroidaceae and a non-limiting example of a *Bacteroides* species is *B. fragilis*.

"*Faecalibacterium*" as used herein refers to a genus of bacteria of which its sole known species, *Faecalibacterium prausnitzii* is gram-positive, mesophilic, rod-shaped, anaerobic and is one of the most abundant and important commensal bacteria of the human gut microbiota. It is non-spore forming and non-motile. These *Faecalibacterium* bacteria produce butyrate and other short-chain fatty acids through the fermentation of dietary fiber.

Over the past decade, real-time polymerase chain reaction (RT-PCR) methods have been used to detect the presence of various microbial pathogens through the amplification of specific DNA sequences without culturing bacteria. One study has measured the amount of *Bacteroides* by using qPCR to quantify the host-specific 16S rRNA genetic marker (Layton et al 2006 App Environ Microbiol 72:4214-4224).

As used herein, the term "patient" or "individual" or "subject" typically denotes humans, but may also encompass reference to non-human animals, preferably warm-blooded animals, more preferably mammals, such as, e.g. non-human primates, rodents, canines, felines, equines, ovines, porcines, and the like.

As used herein, the term "gut" generally comprises the stomach, the colon, the small intestine, the large intestine, cecum and the rectum. In addition, regions of the gut may be subdivided, e.g. the right versus the left side of the colon may have different microflora populations due to the time required for digesting material to move through the colon, and changes in its composition in time. Synonyms of gut include the "gastrointestinal tract", or possibly the "digestive system", although the latter is generally also understood to comprise the mouth, esophagus, etc.

Quantifying cells such as microbial cells in a sample is a method well known for the skilled person. Examples for this can be found in Vandeputte et al 2017 (Nature 551: 507-511) which is incorporated as reference herein. Also the determination of the microbiome composition/profile to unravel the relative abundance of bacterial genera such as the *Bacteroides* and/or *Faecalibacterium* genus in a stool sample are standard methods especially in the field of gut microbiome analysis. In a particular embodiment, the microbiome composition or the microbiome profile in a stool sample is determined using microbiota phylogenetic profiling.

The term "gut microbiome composition" is equivalent in wording as "gut microbiome profile" and these wordings are used interchangeably herein. A gut microbiome profile represents the presence, absence or the abundance of one or more of bacterial genera identified in a stool sample. The gut microbiome profile can be determined based on an analysis of amplification products of DNA and/or RNA of the gut microbiota, e.g. based on an analysis of amplification products of genes coding for one or more of small subunit rRNA, etc. and/or based on an analysis of proteins and/or metabolic products present in the biological sample. Gut microbiome profiles may be "compared" by any of a variety of statistical analytic procedures. Detection of microbial genera may be done in any of a number of ways that are known to those of ordinary skill in the art, including but not limited to culturing the organism or the few organisms, conducting various analyses which are indicative of the presence of the microbe(s) of interest (e.g. by microscopy, using staining techniques, enzyme assays, antibody assays, etc.), or by sequencing of genetic material (DNA or RNA), and others. However, generally it will be beneficial to obtain as much information as possible (or at least more information) regarding the microflora present in the sample. Older techniques (e.g. cultivation) are generally impractical for such an undertaking. Thus, newer nucleic acid sequencing technology (NextGen technology) is usually used. While any category (or categories) of nucleic acid(s) may be detected (usually amplified using, e.g. PCR techniques), particularly useful amplification strategies include the use of primers (e.g. universal primers) which amplify ribosomal RNA genes (rRNA). Such techniques and primers are well-known to those of skill in the art, e.g. see: Quince et al., "Accurate determination of microbial diversity from 454 pyrosequencing data", Nature methods 6.9 (2009): 639-641; Whiteley et al., "Microbial 16S rRNA Ion Tag and community metagenome sequencing using the Ion Torrent (PGM) Platform", Journal of microbiological methods 91.1 (2012): 80--88; Caporaso et al. 2012, "Ultra-high-throughput microbial community analysis on the Illumina HiSeq and MiSeq platforms", ISME J.; Kozich et al., "Development of a dual-index sequencing strategy and curation pipeline for analyzing amplicon sequence data on the MiSeq Illumina sequencing platform", Applied and environmental microbiology 79.17 (2013): 5112-5120; of which the complete contents are hereby incorporated by reference. Standardly, the 16S sequence or a portion of the 16S sequence is used for this purpose but any other sequence or the entire genome can be used (e.g. a functionally conserved housekeeping gene found broadly across the eubacterial kingdom). In microbiology, "16S sequencing" or "16S" refers to a sequence derived by characterizing the nucleotides that comprise the 16S ribosomal RNA gene(s). The bacterial 16S rRNA is approximately 1500 nucleotides in length and is used in reconstructing the evolutionary relationships and sequence similarity of one bacterial isolated to another using phylogenetic approaches. In more particular embodiments, said phylogenetic profiling is performed using PCR, reverse transcriptase (RT)-PCR, quantitative (q)PCR, multiplex PCR, high-throughput sequencing, metatranscriptomic sequencing, identification of strain-specific markers and/or 16S rRNA analysis. In other particular embodiments, said microbiome profile of a subject is the subject's gut enterotype.

Concerning the methods disclosed herein, after a sample, more particularly a fecal or stool sample is obtained, the types and/or the quantity (e.g. occurrence or abundance) in the sample of a multitude or plurality of bacteria, particularly of at least 2, 3, 4, 5, 6, 7, 8, 9, 10 or 20 bacterial genera, more particularly of at least 30, 40 or 50 bacterial genera, even more particularly of at least 100 bacterial genera, most particularly of all detectable bacteria in the sample is determined according to any method known to those of skill in the art. In addition, a total amount of bacteria may be determined, and then for each constituent bacteria, a fractional percentage (e.g. relative amount, ratio, distribution, frequency, percentage, etc.) of the total is calculated. The result is typically correlated with at least one suitable control result, e.g. control results of the same parameter(s) obtained from asymptomatic individuals (negative control), and/or individuals known to have an inflammatory disorder (positive control), or from subjects who have had an inflammatory disorder and are being or have been treated, either successfully or unsuccessfully, etc.

In some embodiments, what is determined is the abundance of microbial genera within the microbiome. However, characterization may be carried to more detailed levels, e.g. to the level of species, and/or to the level of strain or variation (e.g. variants) within a species, if desired (including the presence or absence of various genetic elements such as genes, the presence or absence of plasmids, etc.). Alternatively, higher taxonomic designations can be used such as Family, Phyla, Class, or Order. The objective is to identify which bacteria are present in the sample from the individual and the relative abundance of those microbes, e.g. expressed as a percentage of the total number of microbes that are present, thereby establishing a microbiome profile or signature for the individual being tested, e.g. for the region of the gut that has been sampled, or for the type of sample that is analyzed.

The term "abundance" as used herein refers to the "amount" or "quantity" of a particular genus of gut microbiota.

As mentioned above, the gut microbiome of a subject is profiled by detecting the bacterial genera in a stool sample of said subject. For example, but without the purpose of being limiting, this can be done by 16S rRNA sequencing. In alternative embodiments, the data retrieved by these profiling analyses can be modeled together with data retrieved from healthy subjects, preferably more than 50, more preferably more than 100, even more preferably more than 200, most preferably more than 500. Using a Dirichlet-multinomial models (DMM) approach on a joint matrix of patient and healthy subject samples, the samples can then be classified into four enterotypes, i.e. *Bacteroides*1, *Bacteroides*2, *Prevotella* and *Ruminococcaceae* (Vandeputte et al 2017 Nature 551:507-511). The different enterotypes are thus per definition gut microbiome profiles. In the application it is disclosed that a patient whose stool sample classifies in the *Bacteroides*2 enterotype can be diagnosed with an inflammatory disorder. Therefore, in a second aspect, a method of detecting an inflammatory disorder in a subject is provided, said method comprising detecting whether a stool sample of said subject is characterized by a *Bacteroides*2 enterotype. In one embodiment, a method of detecting an inflammatory disorder in a subject is provided, said method comprising:

a. Clustering n stool samples in 4 distinct enterotypes based on microbiota phylogenetic profiling, wherein said stool samples are derived from n different healthy individuals and wherein n is more than 50;

b. Classifying a stool sample of said subject in one of said distinct enterotypes based on microbiota phylogenetic profiling;

c. Detecting an inflammatory disorder in said subject if said stool sample of said subject is classified as a *Bacteroides*2 enterotype.

Alternatively phrased, a method is provided to indicate a high probability of a patient or test subject developing or having an inflammatory disorder, said method comprising:
a. Clustering n stool samples in 4 distinct enterotypes based on microbiota phylogenetic profiling, wherein said stool samples are derived from n different healthy individuals and wherein n is more than 50;
b. Determining or classifying a stool sample of said patient or test subject as one of said distinct enterotypes based on microbiota phylogenetic profiling;
c. Diagnosing a high probability of said patient or test subject developing or having an inflammatory disorder if said stool sample of said patient or test subject is determined or classified as a *Bacteroides*2 enterotype.

In particular embodiments of the methods of the second aspect, said *Bacteroides*2 enterotype is characterised by low microbial cell count and overrepresentation of the *Bacteroides* genus and/or underrepresentation of the *Faecalibacterium* genus. In even more particular embodiments, said *Bacteroides*2 enterotype is characterised by a lower microbial cell count and a higher relative fraction of *Bacteroides* genus and/or lower relative fraction of *Faecalibacterium* genus compared to a *Prevotella* or *Ruminococcaceae* enterotype or to that of a stool sample of a healthy subject. In other particular embodiments, said *Bacteroides*2 enterotype is characterised by low microbial cell count, an overrepresentation of the *Bacteroides* genus and an underrepresentation of the *Faecalibacterium* genus. In most particular embodiments, said clustering is done using Dirichlet-multinomial models. In other particular embodiments, n is more than 100, more than 200, more than 300, more than 400, more than 500, more than 600, more than 700, more than 800, more than 900 or more than 1000.

In particular embodiments of the second aspect, said low microbial cell count is a cell count of less than $1.5 \times 10^{11}$ or less than $1 \times 10^{11}$ cells per gram stool. In other particular embodiments said low microbial cell count is a microbial cell count which is at least 10%, at least 50%, at least 2 fold or at least 10 fold lower than the microbial count of a stool sample of a healthy subject.

"Overrepresentation of the *Bacteroides* genus" means that the *Bacteroides* genus belongs to the 25%, 10%, 5%, 3%, 2% or 1% most abundant genera in said stool sample of said subject or said patient. "Underrepresentation of the *Faecalibacterium* genus" means that the *Faecalibacterium* genus belongs to the 25%, 10%, 5%, 3%, 2% or 1% least abundant genera in said stool sample of said subject or said patient.

In most particular embodiments, a method is provided to indicate a high probability of a patient or test subject developing or having an inflammatory disorder, said method comprising:
a. Clustering n stool samples in 4 distinct enterotypes based on microbiota phylogenetic profiling, wherein said stool samples are derived from n different healthy individuals and wherein n is more than 50;
b. Determining or classifying a stool sample of said patient or test subject as one of said distinct enterotypes based on microbiota phylogenetic profiling;
c. Diagnosing a high probability of said patient or test subject developing or having an inflammatory disorder if said stool sample of said patient or test subject is determined or classified as a *Bacteroides*2 enterotype, wherein said *Bacteroides*2 genotype is defined by a microbial cell count of $1 \times 10^{11}$ cells per gram stool or less and by the presence of the *Bacteroides* genus which belongs to the 10% most abundant genera in said stool sample and/or the presence of the *Faecalibacterium* genus which belongs to the 10% least abundant genera in said stool sample of said subject.

In a third aspect, a method to detect the presence or to assess the risk of development of an inflammatory disease in a patient is provided, comprising the steps of:
determining a gut microbiome profile for said patient, said gut microbiome profile comprising an indication of the microbial cell count and of the relative fractions of at least 20 bacterial genera from a stool sample and comparing said gut microbiome profile of said patient to one or more gut microbiome reference profiles, wherein said one or more gut microbiome reference profiles comprise at least one of a positive gut microbiome reference profile based on results from control subjects with said inflammatory disease and a negative gut microbiome reference profile based on results from control subjects without said inflammatory disease,
if said gut microbiome profile for said patient statistically significantly matches said positive gut microbiome reference profile, then concluding that said patient has or is at risk of developing said inflammatory disease; and/or
if said gut microbiome profile for said patient statistically significantly matches said negative gut microbiome reference profile, then concluding that said patient does not have or is not at risk of developing said inflammatory disease.

In particular embodiments, said gut microbiome profile is determined using a stool sample of said patient and control subjects. In other particular embodiments, said at least 20 bacterial genera is at least 30 bacterial genera, at least 40 bacterial genera, at least 50 bacterial genera, at least 60 bacterial genera, at least 70 bacterial genera, at least 80 bacterial genera, at least 90 bacterial genera or at least 100 bacterial genera. In yet another particular embodiment, said bacterial genera are those that are most abundant in the stool sample of the patient and control subjects. In other particular embodiments, said gut microbiome profile comprises at least an indication of the relative fractions of *Bacteroides* genus and/or of *Faecalibacterium* genus.

Also, a method is provided to detect the presence or to assess the risk of development of an inflammatory disease in a patient, comprising detecting whether the gut enterotype for said patient statistically significantly matches the *Bacteroides*2 enterotype. This is equivalent as saying that methods are provided to detect the presence or to assess the risk of development of an inflammatory disease in a patient, comprising determining the gut enterotype for said patient, said gut enterotype consists of *Bacteroides*1, *Bacteroides*2, *Prevotella* or *Ruminococcaceae;* wherein a *Bacteroides*2 enterotype is indicative for said patient to have or to be at risk of developing an inflammatory disease. In particular embodiments, said gut enterotype is determined using a stool sample of said patient and control subjects.

Thus, once an individual patient's gut microbiome profile or enterotype with respect to the targeted microbes has been determined, it is compared to known reference profiles obtained previously from control experiments. Such control experiments typically obtain "negative control" data from normal (healthy) individuals, i.e. comparable individuals who do not have disease symptoms, and positive control data from comparable individuals who do have the disease in question or particular disease symptoms or did have at the time of the analysis. In particular embodiments, a "positive control data" means a *Bacteroides*2 enterotype, while "negative control data" means *Bacteriodes*1, *Prevotella* or *Ruminococcaceae* enterotype. Based on a comparative analysis between the patient's gut microbiome profile and one or more reference or control microbiome profiles (and usually corroborated statistically by methods that are well-known to those of ordinary skill in the art) the likelihood or risk of the patient for developing the disease or condition of interest is determined and thus can be used as a predictive diagnostic. For example, a person with a profile that is not similar to or within the range of values seen in control profiles which are not associated with disease, but which is more similar to or within ranges determined for disease associated profiles, may be deemed to be at high risk for developing the disease. This is generally the case, for example, if his/her microbiome profile, particularly his/her gut enterotype is associated with the disease state with a statistically significant (P value) of less than about 0.05 (after multiple testing correction).

In other embodiments of the invention, when many genera are being considered, the overall pattern of the gut microbiome is assessed, i.e. not only are particular genera identified, but the percentage of each constituent genus is taken in account, in comparison to all genera that are detected and, usually, or optionally, to each other. Those of skill in the art will recognize that many possible ways of expressing or compiling such data exist, all of which are encompassed by the present invention, for example, the relationships may be expressed numerically or graphically as ratios or percentages of all genera detected, etc. Further, the data may be manipulated so that only selected subsets of the genera are considered (e.g. key indicators with strong positive correlations). Data may be expressed, e.g. as a percentage of the total number of microbes detected, or as a weight percentage, etc.

In one embodiment, a nonparametric multivariate test such as Metastats, Analysis of Similarity, Principle Component Analysis, Non-Parametric MANOVA (Kruskal-Wallace), or other tests known by the skilled person, can be used to associate microbiome dysbiosis with a statistical significant (P value) of less than 0.05 (after multiple testing correction). Such tests are known in the art and are described, for example, by White et al., "Statistical methods for detecting differentially abundant features in clinical metagenomic samples", PLoS Comput Biol 5.4 (2009): e1000352; Segata et al., "Metagenomic biomarker discovery and explanation", Genome Biol 12.6 (2011): R60.

In other embodiments, phylogenetic methods such as Unifrac can be used to associate microbiome profiles with the disease state with a statistically significant (P value) of less than 0.05 (after multiple testing correction). See, for example, Lozupone C, Knight R (2005) UniFrac: a new phylogenetic method for comparing microbial communities. Appl Environ Microbiol 71:8228-8235.

In other embodiments, still other methods can be used to associate microbiome profiles with the disease state with a statistically significant (P value) of less than 0.05 (after multiple testing correction). See for example: Linear models (MaAsLin—Tickle T, Waldron L, Yiren Lu, Huttenhower C. Multivariate association of microbial communities with rich metadata in high-dimensional studies, e.g. as in Morgan et al. Genome Biol 2015, 16:67); Machine Learning tools such as Random Forests, Support Vector Machines; ecological visualization tools (vegan: Community Ecology Package. R Package [Internet]. 2015 J Oksanen, F Blanchet, R Kindt, P Legendre, P Minchin, R O'Hara), amongst others.

In a fourth aspect, a method of diagnosing and treating an inflammatorydisorder in a patient is provided, said method comprising the steps of:
  a. Diagnosing said subject with an inflammatory disorder when said stool sample is characterized by low cell count and by a high relative fraction of the *Bacteroides* and/or a low relative fraction of the *Faecalibacterium* genus;
  b. Administering an effective amount of anti-inflammatory drugs to the diagnosed patient.

In particular embodiments, a method of diagnosing and treating an inflammatory disorder in a patient is provided, said method comprising the steps of:
  a. Quantifying or measuring the number of bacterial cells in a stool or fecal sample of said subject;
  b. Determining the microbiome composition of said stool sample;
  c. Diagnosing said subject with an inflammatory disorder when said stool sample is characterized by low cell count and by a high relative fraction of the *Bacteroides* and/or a low relative fraction of the *Faecalibacterium* genus;
  d. Administering an effective amount of anti-inflammatory drugs to the diagnosed patient.

An "effective amount" of a composition is equivalent to the dosage of the composition that leads to treatment, prevention or a reduction of the severity of inflammation status in a patient. Said inflammation can be gut inflammation for which several methods are known to the person skilled in the art to evaluate or thus to diagnose the severity of the inflammation.

In most particular embodiments, a method of diagnosing and treating an inflammatory disorder in a patient is provided, said method comprising the steps of:
  a. Diagnosing said subject with an inflammatory disorder when said stool sample is characterized by a microbial cell count of $1 \times 10^{11}$ cells per gram stool or less and by the presence of the *Bacteroides* and/or *Faecalibacterium* genus, wherein the *Bacteroides* genus belongs to the 10% most abundant genera in said stool sample and the *Faecalibacterium* genus belongs to the 10% least abundant genera in said stool sample;
  b. Administering an effective amount of anti-inflammatory drugs to the diagnosed patient.

Also a method of diagnosing and treating an inflammatory disorder in a patient is provided, said method comprising the steps of:
  a. Quantifying or measuring the number of bacterial cells in a stool or fecal sample of said subject;
  b. Determining the microbiome composition of said stool sample;
  c. Diagnosing said subject with an inflammatory disorder when said stool sample is characterized by a microbial cell count of $1 \times 10^{11}$ cells per gram stool or less and by the presence of the *Bacteroides* and/or *Faecalibacterium* genus, wherein the *Bacteroides* genus belongs to the 10% most abundant genera in said stool sample and the *Faecalibacterium* genus belongs to the 10% least abundant genera in said stool sample;
  d. Administering an effective amount of anti-inflammatory drugs to the diagnosed patient.

In particular embodiments of the invention, said stool sample comprises the gut microbiome from a human patient to be diagnosed or from a healthy control.

In another embodiment, a method of diagnosing and treating an inflammatory disease in a patient is provided, comprising the steps of:

determining a gut microbiome profile for said patient, said gut microbiome profile comprising an indication of the microbial cell count and of the relative fractions of at least 20 bacterial genera from a stool sample and comparing said gut microbiome profile of said patient to one or more gut microbiome reference profiles, wherein said one or more gut microbiome reference profiles comprise at least one of a positive gut microbiome reference profile based on results from control subjects with said inflammatory disease and a negative gut microbiome reference profile based on results from control subjects without said inflammatory disease, administering anti-inflammatory therapy to said patient if said gut microbiome profile for said patient statistically significantly matches said positive gut microbiome reference profile.

In particular embodiments, said gut microbiome profile is determined using a stool sample of said patient and control subjects. In other particular embodiments, said at least 20 bacterial genera is at least 30 bacterial genera, at least 40 bacterial genera, at least 50 bacterial genera, at least 60 bacterial genera, at least 70 bacterial genera, at least 80 bacterial genera, at least 90 bacterial genera or at least 100 bacterial genera. In yet another particular embodiment, said bacterial genera are those that are most abundant in the stool sample of the patient and control subjects. In particular embodiments, said at least 20 bacterial genera comprises the *Bacteroides* genus and/or the *Faecalibacterium* genus.

Also, a method is provided of diagnosing and treating an inflammatory disease in a patient, comprising administering anti-inflammatory therapy to said patient if the gut enterotype for said patient statistically significantly matches the *Bacteroides*2 enterotype. This is equivalent as saying that methods are provided to diagnose and treat an inflammatory disease in a patient, comprising determining the gut enterotype for said patient, said gut enterotype consists of *Bacteroides*1, *Bacteroides*2, *Prevotella* or *Ruminococcaceae*; and administering anti-inflammatory therapy to said patient if said gut enterotype of said patient is a *Bacteroides*2 enterotype. In particular embodiments, said gut enterotype is determined using a stool sample of said patient and control subjects.

Commonly used anti-inflammatory drugs are inhibitors of cyclooxygenase activity (aspirin, celecoxib, diclofenac, diflunisal, etodolac, ibuprofen, indomethacin, ketoprofen, ketorolac, meloxicam, nabumetone, naproxen, oxaprozin, piroxicam, salsalate, sulindac, tolmetin, among others) or corticosteroids (prednisone, dexamethasone, hydrocortisone, methylprednisolone, among others) or in combination with commonly used analgesics (acetaminophen, duloxetine, paracetamol, among others) or in any combination thereof. In particular embodiments, said anti-inflammatory therapy includes a biological therapy, such as TNF-alpha blockers, anti-IL17A monoclonal antibodies, anti-CD20 antibodies.

The therapeutic options for CD or UC include corticosteroids, aminosalicylates, immunosuppressive agents and biological therapies. Due to the chronic relapsing and remitting disease-course of IBD, the goal of medical therapy is to induce (induction phase) and maintain remission (maintenance phase). The choice between the different medical therapies depends on several factors such as disease location and severity, medical and surgical history, age, co-morbidities, extra-intestinal manifestations and treatment availability (Gomollon et al 2017 J Crohns Colitis 11:3-25; Harbord et al 2017 J Crohns Colitis 2017).

The term "inflammation", "inflammatory disorder" or "inflammatory disease" refers to complex but to the skilled person well known biological response of body tissues to harmful stimuli, such as pathogens, damaged cells, or irritants. However, inflammation is not a synonym for infection. Infection describes the interaction between the action of microbial invasion and the reaction of the body's inflammatory response—the two components are considered together when discussing an infection, and the word is used to imply a microbial invasive cause for the observed inflammatory reaction. Inflammation on the other hand describes purely the body's immunovascular response, whatever the cause may be. Inflammation is a protective response involving immune cells, blood vessels, and molecular mediators. The function of inflammation is to eliminate the initial cause of cell injury, clear out necrotic cells and tissues damaged from the original insult and the inflammatory process, and to initiate tissue repair. The classical signs of inflammation are heat, pain, redness, swelling, and loss of function. Inflammation is a generic response, and therefore it is considered as a mechanism of innate immunity, as compared to adaptive immunity, which is specific for each pathogen. Inflammation can be classified as either acute or chronic. Acute inflammation is the initial response of the body to harmful stimuli and is achieved by the increased movement of plasma and leukocytes (especially granulocytes) from the blood into the injured tissues. A series of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation, such as mononuclear cells, and is characterized by simultaneous destruction and healing of the tissue from the inflammatory process.

In further embodiments of the methods of current applications, said inflammation is associated with at least one of the following disorders or conditions: spondyloarthritis, ankylosing spondylitis, reactive arthritis, psoriatic arthritis, enteropathic arthritis, undifferentiated spondyloarthritis, juvenile idiopathic arthritis, primary sclerosing cholangitis, multiple sclerosis, inflammatory bowel disease, Crohn's disease, ulcerative colitis and any combination thereof. In other further embodiments, said inflammatory disorder is a gut inflammatory disorder while said inflammation is gut inflammation.

The wording "gut inflammation" is equivalent to the wording "microscopic gut inflammation" as used herein and refers to an inflammatory response in the gut as defined above. The inflammation can affect the entire gastrointestinal tract, can be more limited to for example the small intestine or large intestine but can also be limited to specific components or structures such as the bowel walls.

In other further embodiments, said gut inflammatory disorder or said gut inflammation is selected from the list consisting of Crohn's disease, irritable bowel syndrome, inflammatory bowel disease (IBD), ulcerative colitis, celiac disease, primary sclerosing cholangitis, multiple sclerosis, spondyloarthritis and gut inflammation associated with primary sclerosing cholangitis, multiple sclerosis or spondyloarthritis.

As used herein, the term "inflammatory bowel disease" or abbreviated "IBD" refers to an umbrella term for inflammatory conditions of the gut under which both Crohn's disease and ulcerative colitis fall. In people with IBD, the immune system mistakes food, bacteria, or other materials in the gut for foreign substances and responds by sending white blood cells into the lining of the bowels. The result of the immune system's attack is chronic inflammation. Crohn's disease and ulcerative colitis are the most common forms of IBD. Less common IBDs include microscopic colitis, diverticulosis-associated colitis, collagenous colitis, lymphocytic colitis and Behçet's disease. In the case of CD, transmural inflammation commonly affects the terminal ileum, although any part of the gastrointestinal system can be affected. Discontinuous inflammation and the presence of non-caveating granulomas are also characteristic of the inflammation in patients with CD. In contrast, UC is characterized by continuous mucosal inflammation starting in the rectum and extending proximally until the caecum (Harries et al 1982 Br Med J Clin Res Ed, 284:706). These are chronic relapsing diseases originating mostly during adolescence and young adulthood and are characterized by chronic inflammation of the gastrointestinal tract leading to invalidating symptoms of bloody diarrhea, weight loss and fatigue (Wilks 1859 Med Times Gazette 2:264-265). The latest epidemiologic data from France reported a mean incidence of 4.4 cases per 100 000 individuals (Ghione et al 2017 Am J Gastroenterol). Worldwide, the incidence and prevalence of CD range from 0.0-29.3 per 100 000 person-years and 0.6-318.5 per 100 000 persons, respectively. The incidence and prevalence of UC varies from 0.0-19.2 per 100 000 person-years and 2.42-298.5 per 100 000 persons, respectively (Molodecky et al 2012 Gastroenterology 142:46-54).

Several defects in innate and adaptive immunity have been described both in UC and CD (de Souza et al 2016 Nat Rev Gastroenterol Hepatol 13:13-27). In normal conditions, intestinal macrophages exhibit inflammatory anergy which allows the interaction with commensal flora without inducing strong inflammatory responses (Smythies et al 2005 J Clin Invest 115:66-75). However, CD14+ intestinal macrophages are more abundant in patients with CD than in healthy individuals. These CD14+ intestinal macrophages produce more proinflammatory cytokines, such as interleukin(IL)-6, IL-23 and tumor necrosis factor (TNF)-a, than the common CD14-intestinal macrophages (Kamada et al 2008 J Clin Invest 118:2269-2280). Adaptive immunity also plays a role in the pathogenesis of IBD. T helper (TH) lymphocytes are cytokine producing lymphocytes that potentiate or regulate immune responses by interacting with other immune cells such as macrophages, CD8+ T cells, eosinophils and basophils. Following an initial trigger (e.g. impaired barrier function by injury or exposure to xenobiotics) the microbe-associated molecular patterns will induce the secretion of cytokines by dendritic cells, epithelial cells and macrophages, among others. Different cytokine milieus will induce TH1, TH2, TH17 or regulatory T-cell (Treg) subsets (de Souza et al 2016 Nat Rev Gastroenterol Hepatol 13:13-27). In susceptible individuals, an interplay between TH1 and TH17 immune responses seem to be linked with inflammation associated with CD. On the other hand, UC has been described as a TH2-like condition with possible implication of a newly discovered TH9 lymphocytes (de Souza et al 2016 Nat Rev Gastroenterol Hepatol 13:13-27; Gerlach et al 2014 Nat Immunol 15:676-686). In both diseases, an insufficient Treg response seems to be involved in the impaired regulation of inflammatory responses (Maul et al 2005 Gastroenterology 128:1868-1878). In active IBD, the immune system shows an increased response to bacterial stimulation, thereby contributing even further to the chronic inflammatory state. This inflammatory state also produces an increase in the intestinal permeability, allowing bacterial antigens to contact with the immune system, hereby perpetuating the inflammatory state.

In particular embodiments, said inflammation or inflammatory disorder as used in the methods of current application is inflammation or an inflammatory disorder characterized by a TH1, TH17, TH2 and/or TH9 response. In even more particular embodiments, said inflammation or inflammatory disorder is characterized by a TH1 and/or TH17 response.

As used herein, the term "spondyloarthritis" or abbreviated "SpA" refers to a group of closely related, but clinically heterogeneous, inflammatory arthritis diseases with common features, including inflammation of the spine, eyes, skin, joints and gastrointestinal tract. This SpA group is also sometimes referred to as spondylitis and spondyloarthropathies. As used herein, SpA includes ankylosing spondylitis (including non-radiographic axial SpA, i.e. ankylosing spondylitis diagnosed using MRI), reactive arthritis, psoriatic arthritis, enteropathic arthritis (arthritis associated with inflammatory bowel disease or IBD related arthritis), undifferentiated spondyloarthritis, juvenile idiopathic arthritis and juvenile-onset SpA. Characteristics of these SpA diseases include inflammatory arthritis of the spine, peripheral arthritis that differs from rheumatoid arthritis, extra articular manifestations of inflammatory bowel disease, arthritis and uveitis, seronegativity for rheumatoid factor and some degree of heritability, including the presence of the gene HLA-B27. It is thus clear that in current application SpA is not rheumatoid arthritis.

"Primary sclerosing cholangitis" or "PSC" as used herein refers to a severe chronic liver disease characterized by progressive biliary inflammation and fibrosis. The development of multifocal bile duct structures can lead to liver fibrosis and subsequent cirrhosis. Patients with PSC are usually asymptomatic and the diagnostic work up is triggered by incidental findings of altered liver enzymes. In symptomatic patients, fatigue, pruritus, abdominal pain and jaundice are the most reported symptoms (Lazaridis et al 2016 N Engl J Med 375:1161-1170). Following clinical suspicion and a suggestive biochemistry, magnetic resonance cholangiography or endoscopic retrograde cholangiopancreatography are used to establish the diagnosis. Presently, liver biopsy is reserved to diagnose suspected small duct PSC or to exclude other diagnosis (Lindor et al 2015 Am J Gastroenterol 110:646-659). It would thus be highly advantageous to develop presymptomatic diagnostic methods or non-invasive diagnostic methods. The diagnostic methods disclosed above solve this technical problem. Therefore, in a particular embodiment, all method disclosed in this application are method of diagnosing primary sclerosing cholangitis, more particularly gut inflammation associated with primary sclerosing cholangitis.

A systematic review of the epidemiologic studies in PSC reported an incidence varying between 0 and 1.3 cases per 100 000 individuals and a prevalence of 0-16.2 cases per 100 000 individuals (Boonstra et al 2012 J Hepatol 56:1181-1188). Most commonly, PSC affects men at the age of 40 and the concomitant diagnose of IBD is very common. Between 60 to 80% of the patients with PSC have concomitantly IBD, most frequently UC, pointing towards the possible role of the colon in the pathogenesis of PSC (Boonstra et al 2013 Hepatology 58:2045-2055). In patients with IBD, the prevalence of PSC varies from 0.4 to 6.4%. However, in a recent study using magnetic resonance to diagnose PSC in patients with IBD the prevalence of PSC was 3-fold higher than previously reported, mainly due to subclinical PSC without symptoms or altered liver enzymes (Lunder et al 2016 Gastroenterology 151:660-669).

Genome-wide association studies suggested a role for immune-related pathways in the pathogenesis of PSC. Patients with PSC have a higher activity of TH17 cells. These lymphocytes help in the defence against bacteria and fungi by promoting inflammation and are involved in auto-immune diseases (Katt et al 2013 Hepatology 58:1084-1093. Moreover, Treg cells (CD4+CD25+FOXP3+CD127−), which suppress inflammation, are reduced in PSC (Sebode et al 2014 J Hepatol 60:1010-1016). Therefore, in a very particular embodiment, the inflammatory disorder as mentioned in the application refers to inflammatory disorders characterized by a TH17 response.

The majority of patients with PSC have concomitant IBD, pointing towards the possible role of the colon in the pathogenesis of PSC. This role is further evidenced by transplantation data showing that colectomy before liver transplantation is a protective factor for recurrence of PSC after liver transplantation (Alabraba et al 2009 Liver Transpl 15:330-340). Interestingly, the absence of intestinal microbiota is associated with increased severity of the disease in mice model (Tabibian et al 2016 Hepatology 63:185-196). Therefore, intestinal microbiota may play an important role in the pathogenesis of PSC by modulating the gut-associated immune system to a more immunogenic or tolerogenic phenotype.

"Multiple sclerosis" or "MS" as used herein refers to a chronic inflammatory and neurodegenerative disease characterized by substantial clinical heterogeneity. Both genetic and immunologic factors, as well as environmental elements contribute to its aetiology. Most MS patients present with recurrent periods of relapses and remissions, with relapses thought to be provoked by the infiltration of adaptive immune cells into the central nervous system (CNS), hereby resulting in focal inflammation and myelin loss (Franciotta et al 2008 Lancet neurology 7:852-588). In a minority of patients, slow progression is observed from onset. Therefore, three clinical phenotypes can be distinguished: relapsing-remitting (RR), secondary progressive (SP) or primary progressive (PP) MS. Lublin et al (2014 Neurology 83:278-286) further described these phenotypes as active, not active, and with or without progression. While not recognized as a separate phenotype, a subset of RRMS patients appears to have a mild course, often referred to as benign MS (BMS) (Amato et al 2006 J Neurol 253:1054-1059; Calabrese et al 2013 Mult Scler 19:904-911). Patients experience a wide variety of symptoms, ranging from physical and cognitive symptoms to even bowel dysfunction, with the latter being reported in more than 70% of cases (Wiesel et al 2001 Eur J Gastroenterol Hepatol 13:441-448). Studies in experimental allergic encephalomyelitis (EAE), a widely used mouse model for MS, have provided evidence for a substantial effect of gut microbiota on central nervous system (CNS)-specific autoimmune disease (Berer et al 2014 FEBS letters 588:4207-4013). The absence of gut microbes (germ-free conditions) or the alteration of the gut microbial flora composition with antibiotics resulted in a shift in T cell responses (decreased concentration of IL-17, increased number of regulatory T and B cells) and affected disease severity (Ochoa-Reparaz et al 2009 J Immunol 183:6041-6050). Additionally, mice raised in a germ-free environment were highly resistant to developing spontaneous EAE, unless exposed to specific pathogen-free condition-derived fecal material or a fecal transplant from MS twin-derived microbiota (Berer K et al 2011 Nature 479:538-541; Berer et al 2017 Proc Nat Ac Sc USA). Immune cells from mouse recipients of MS-twin samples produced less IL-10 than immune cells from mice colonized with healthy-twin samples. IL-10 may have a regulatory role in spontaneous CNS autoimmunity, as neutralization of the cytokine in mice colonized with healthy-twin fecal samples increased disease incidence. This evidence suggests that the microbiota may be capable of altering the individual at a phenotypic level and influence the onset, severity and progression of MS. Therefore, in a particular embodiment, the methods disclosed above are methods of detecting multiple sclerosis or gut inflammation associated with multiple sclerosis.

In particular extensions of the above aspects and embodiments, the stool sample of said subject to be diagnosed for an inflammatory disease is further characterized by a lower bacterial diversity compared to a stool sample of a healthy subject. More particularly, said stool sample is even further characterized by the absence of *Escherichia coli* and/or the *Prevotella*.

The following examples are intended to promote a further understanding of the invention. While the invention is described herein with reference to illustrated embodiments, it should be understood that the invention is not limited hereto. Those having ordinary skill in the art and access to the teachings herein will recognize additional modifications and embodiments within the scope thereof. Therefore, the invention is limited only by the claims attached herein.

EXAMPLES

Example 1: Disease-Associated Dysbiosis is Captured by Enterotyping

We capitalized on the power of a population-wide microbiome profiling database from the Flemish Gut Flora Project (FGFP) (Falony et al. 2016 Science 352:560-564) to assess the distribution of 104 PSC/IBD samples in a non-clinical microbiome community space. Using a Dirichlet-multinomial models approach on a joint matrix of patient and FGFP samples, we observed patient samples to fan out over the four previously identified FGFP enterotypes. Patients did separate from their healthy age-, gender-, and BMI-matched FGFP controls (Healthy Controls, HC), as visualised on the first axis of a principal coordinates analysis (PCoA) of inter-individual differences in microbiome composition (FIG. 1a; 66 FGFP HCs were matched with PSC and PSC-IBD patients). Accordingly, diverging enterotype distributions were found associated with disease diagnoses (Chi-square test; FIG. 1b). While 13% of FGFP samples were community-typed as Bacteroides2, the prevalence of this B2 enterotype ranged from 38% in case of UC patients over 60% in PSC patients to 78% in case of CD, with combined phenotypes within this range in the PSC/IBD patient groups (FIG. 1b).

Our analyses show that both PSC and IBD were associated with community-wide shifts in composition that could only be captured by enterotyping when contrasted with non-clinical microbiome variation.

Example 2. Intestinal Inflammation is Associated with Reduced Fecal Cell Counts

Figure 2:
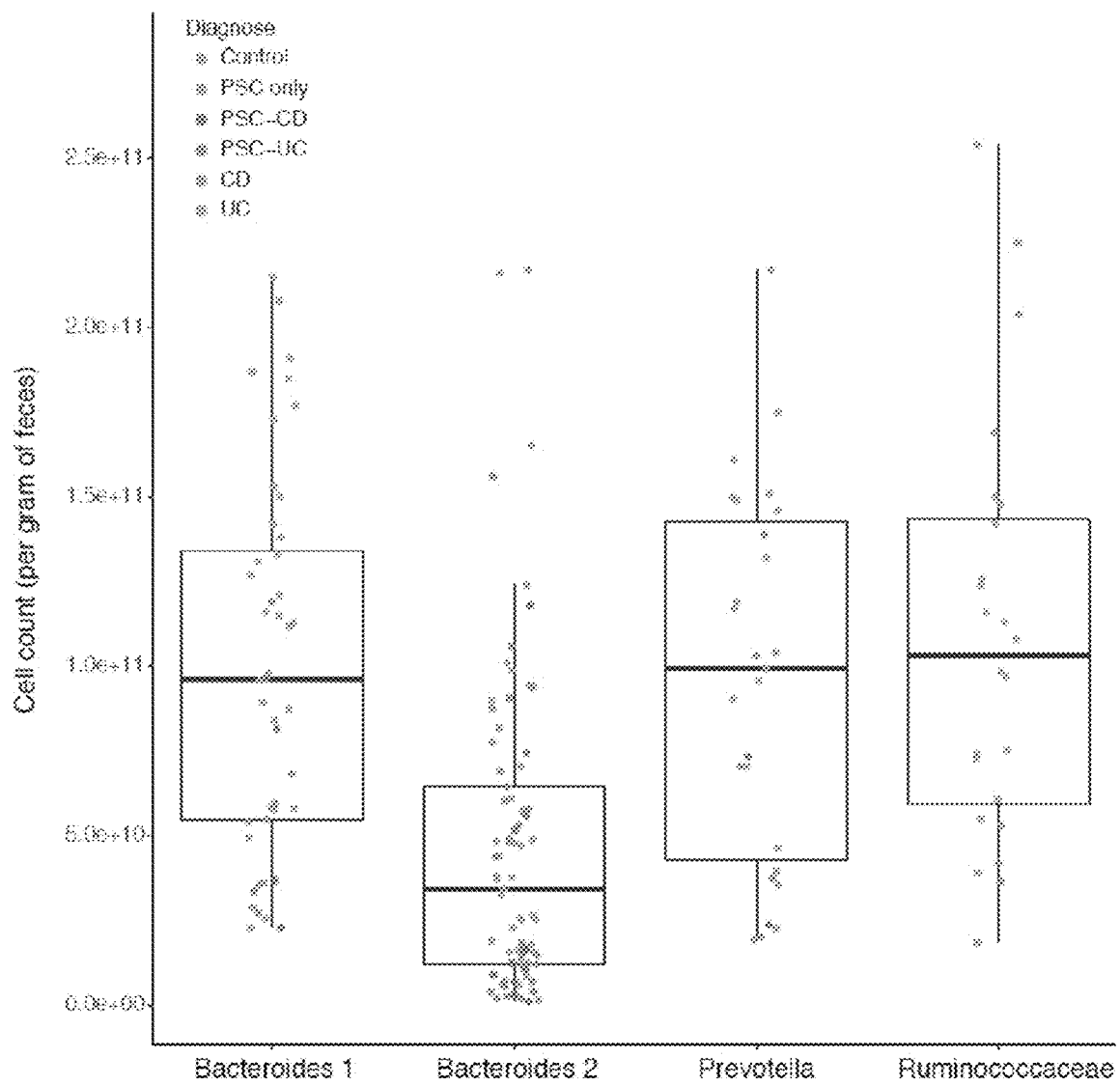
FIG. 2. Microbial load (cell counts) according to enterotype (N=165). Different diagnosis are represented by different colours. Control (red); PSC, primary sclerosing cholangitis (yellow); PSC-CD (green); PSC-UC (blue); CD, Crohn's disease (purple); UC, ulcerative colitis (pink).
Figure 3B:
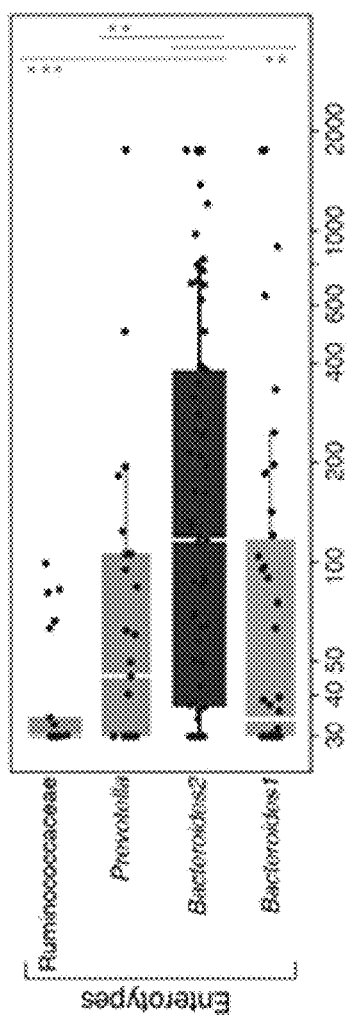
FIG. 3. Associations between PSC/IBD diagnosis, fecal cell counts, and inflammation burden. (a) Variation in microbial load across patients groups in the PSC/IBD/HC cohort (N=170). (b) Intestinal inflammation distribution across enterotypes, as measured by fecal calprotectin (N=159. (c) Correlation between fecal calprotectin and microbial loads (N=161; Spearman rho=p31 0.215, p-value=6e10$^{-3}$). (a,b) Kruskal-Wallis with post-hoc Dunn test, patient groups versus controls, FDR<0.001(*); <0.01(); <0.05(*).
Figure 3C:
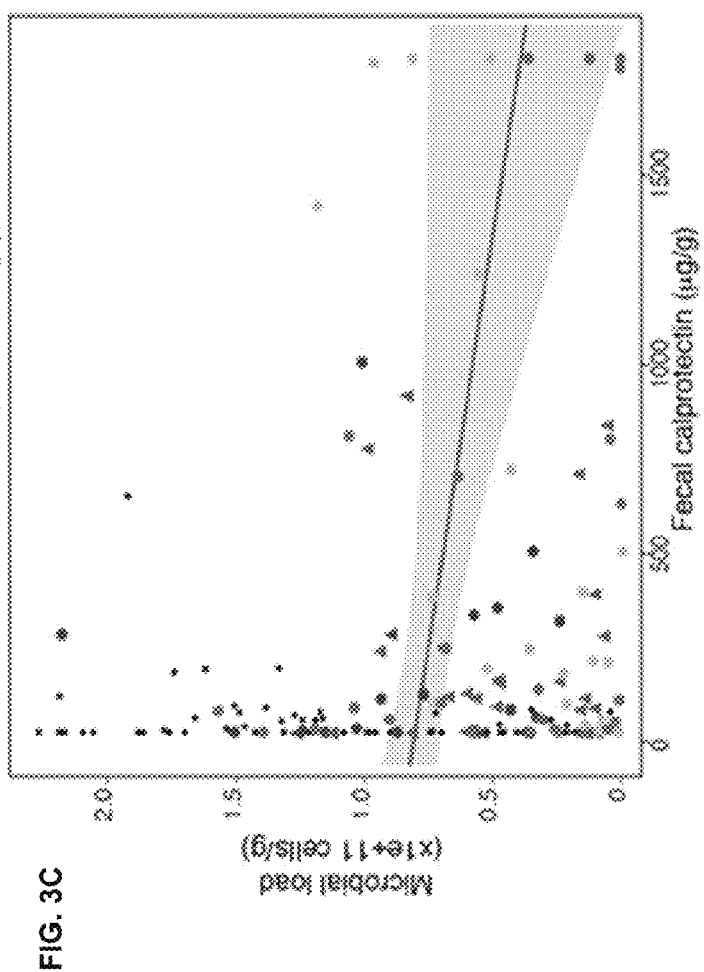
Figure 3A:
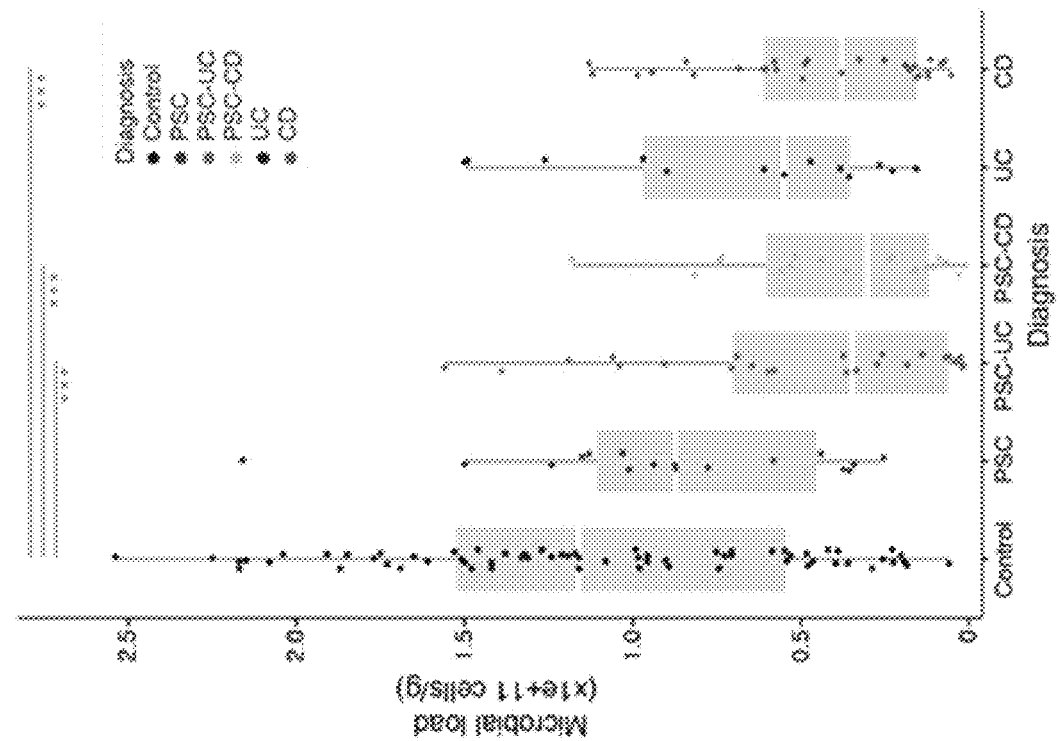

We previously observed significant variation in microbiota density even in healthy individuals and its impacts on microbiota analyses (Vandeputte et al 2017 Nature doi: 10.1038/nature24460). Therefore, we applied the same protocol to measure the total microbial cell counts per gram of fecal sample (fresh weight) from the PSC and IBD cohort. We first observe a strong correlation between observed microbiota richness and sample cell density (Spearman rho=0.87, p-value=5e−51). We confirm, as we previously reported (Vandeputte et al 2017 Nature doi:10.1038/nature24460), that the *Bacteroides*2 enterotype has significantly lower microbiota density than the *Bacteroides*1, *Prevotella* and *Ruminococcaceae* enterotypes (Kruskal-Wallis with post-hoc Dunn test FDR<0.001 (FIG. 2). We now also observe that patients with PSC and concomitant IBD (UC/CD) have 3-fold lower cell count than healthy controls (FDR<0.001; FIG. 3*a*), which is similar to the decrease in CD patients without PSC (FDR<0.001).

Figure 4:
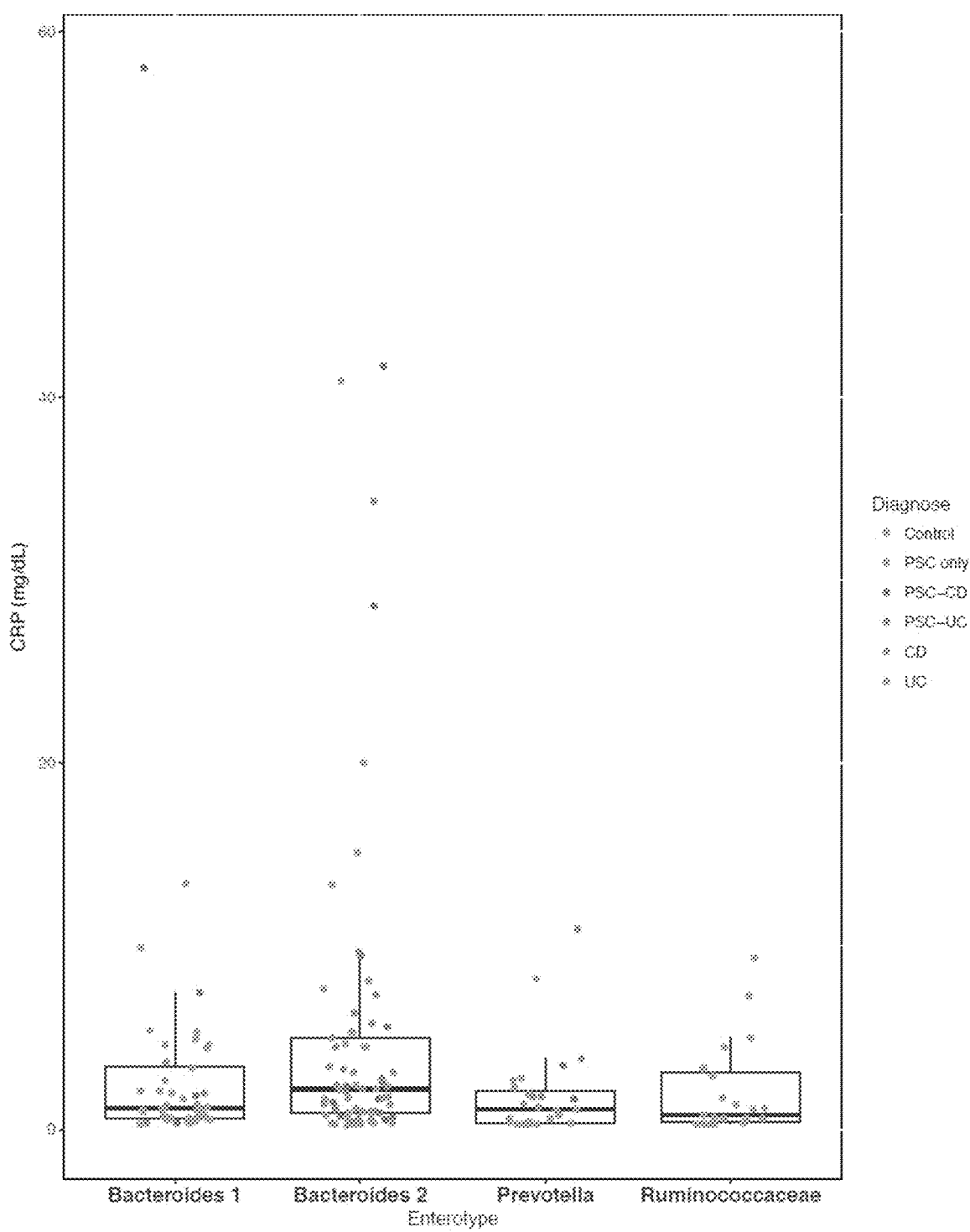
FIG. 4. Distribution of CRP according to enterotype. CD, Crohn's disease; CRP, C-reactive protein; PSC, primary sclerosing cholangitis; UC, ulcerative colitis. Control (red); PSC, primary sclerosing cholangitis (yellow); PSC-CD (green); PSC-UC (blue); CD, Crohn's disease (purple); UC, ulcerative colitis (pink).

Following up on the latter and based on the pathology of the conditions studied, we set out to investigate a potential link between cell counts and host inflammation status. Intestinal inflammation presents differently in UC, characterized by continuous mucosal inflammation, and CD, characterized by discontinuous transmural inflammation. We indeed observe that the systemic inflammation marker CRP differs significantly between enterotypes (Kruskal-Wallis p-value 0.0369; FIG. 4). The association with fecal calprotectin—a marker for intestinal (as opposed to systemic) inflammation—is stronger (Kruskal-Wallis p-value 1.89× $10^{-5}$). Fecal calprotectin is significantly increased in *Bacteroides*2 samples compared to each one of the other enterotypes (FIG. 3*b*).

Figure 5:
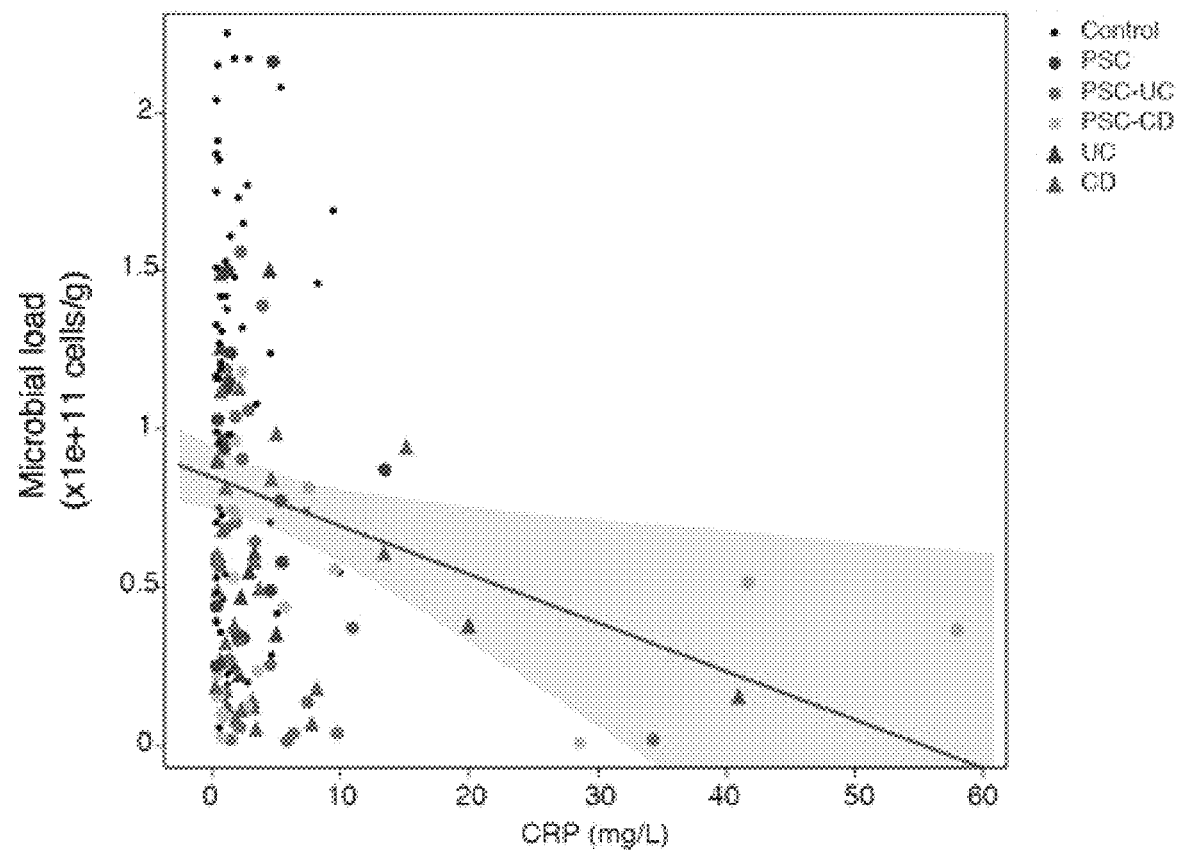
FIG. 5. Serum CRP concentrations correlate with fecal microbial loads. Correlation between CRP and microbial loads in the combined dataset of PSC/IBD patients and healthy controls (N=163, Spearman rho=−0.27, two-sided p-value=6e−4). Control (block dot); PSC, primary sclerosing cholangitis (brown dot); PSC-CD (yellow dot); PSC-UC (orange dot); CD, Crohn's disease (light blue triangle); UC, ulcerative colitis (dark blue triangle).
Figure 6:
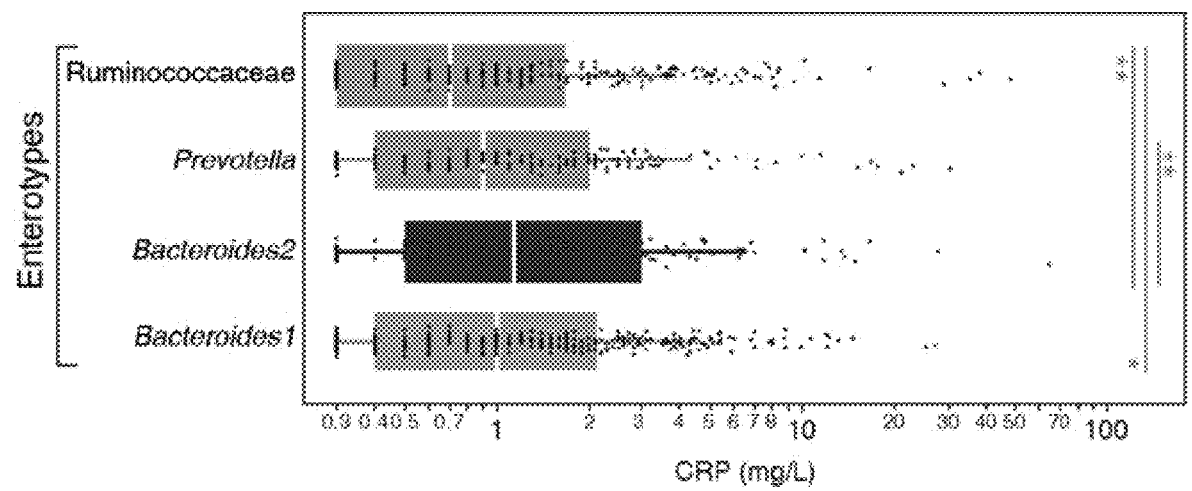
FIG. 6. Serum CRP concentrations also vary across enterotypes in a non-clinical population. Systemic inflammation distribution across enterotypes as measured by serum CRP in the FGFP dataset (N=1120).

In addition, both calprotectin (Pearson log-transformed, N=161, r=−0.24, p-value=2e−03; FIG. 3*c*) and CRP (N=163, r=−0.27, p-value=6e−04; FIG. 5) concentrations negatively correlated with fecal cell counts. A DMM-based reanalysis of the FGFP dataset showed that the link between B2 and systemic inflammation also exists in healthy individuals (Kruskal-Wallis p-value=2e−03; FIG. 6; FGFP calprotectin concentrations were only available for matched controls).

Example 3. PSC Microbial Signature Revisited with QMP

In our original RMP analysis aiming at unveiling the microbiota signature of PSC with or without concomitant IBD, we found, as later reported in other studies (Kummen et al 2017 Gut 66:611-619; Iwasawa et al 2017 Gut p1344-1346) that microbiota diversity (Shannon diversity) was decreased in patients with PSC and patients with CD as compared to healthy (RMP Post-hoc Dunn's test FDR corrected p-value<0.05). One surprising observation was that the intestinal microbial diversity at genus level of patients with PSC without IBD was significantly higher than healthy controls (RMP Tukey multiple comparisons of means test FDR=0.007). Now taking sample cell density into account (QMP), we instead find that intestinal microbial diversity is significantly lower in patients with PSC and concomitant IBD and in patients with CD (Post-hoc Dunn's test FDR<0.05), and not significantly decreased in patients with PSC without IBD (Post-hoc Dunn's test FDR corrected p-value 0.7). However, with QMP analysis there was no significant difference in microbiota diversity between healthy controls and patients with PSC without IBD (Post-hoc Dunn's test FDR=0.149).

Figure 8A:
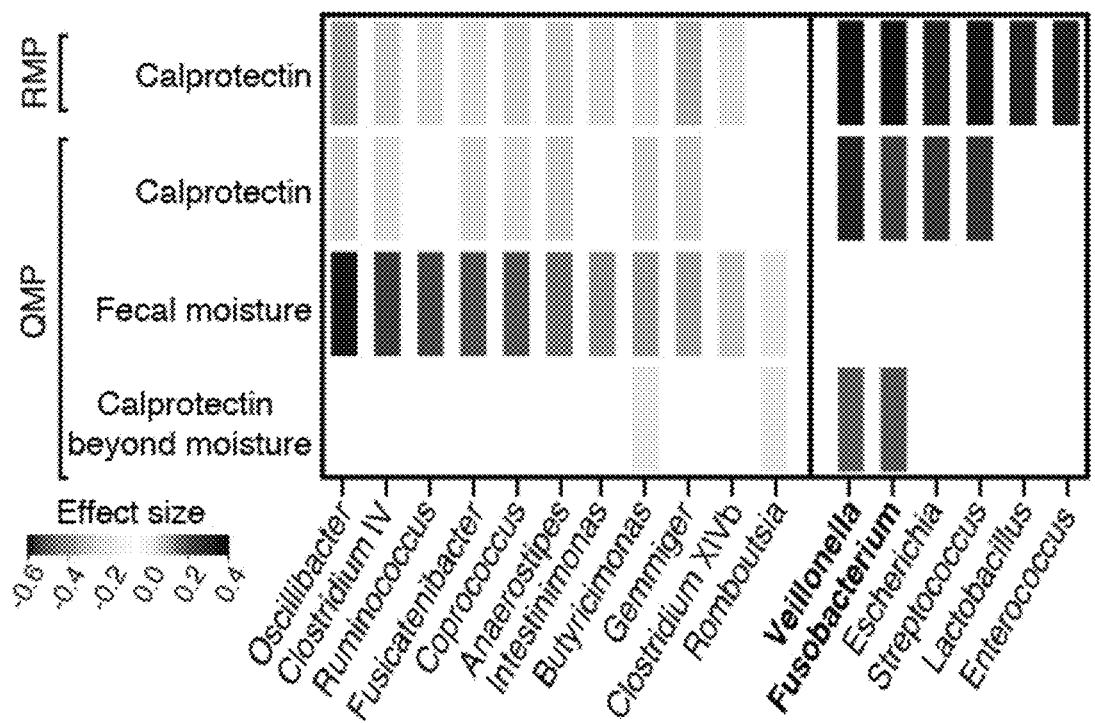
FIG. 8. Quantitative genera profiles associated to inflammatory burden and their coexclusion pattern in the PSC/IBD cohort. (a) Significant correlations between genera RMP (81 taxa) and QMP (63 taxa) abundances and faecal calprotectin concentrations (RMP N=159, QMP N=149 PSC/IBD/HC cohort; Spearman) or moisture content (RMP N=153, QMP N=143 PSC/IBD/HC cohort), and identification of QMP genera abundances correlating with calprotectin beyond moisture content (QMP N=133 PSC/IBD/HC cohort; nested GLM ANOVA). (b) Coexclusion pattern observed between the only two genera significantly positively associated to gastrointestinal inflammatory burden after deconfounding for moisture content—*Veillonella* and *Fusobacterium*.
Figure 8B:
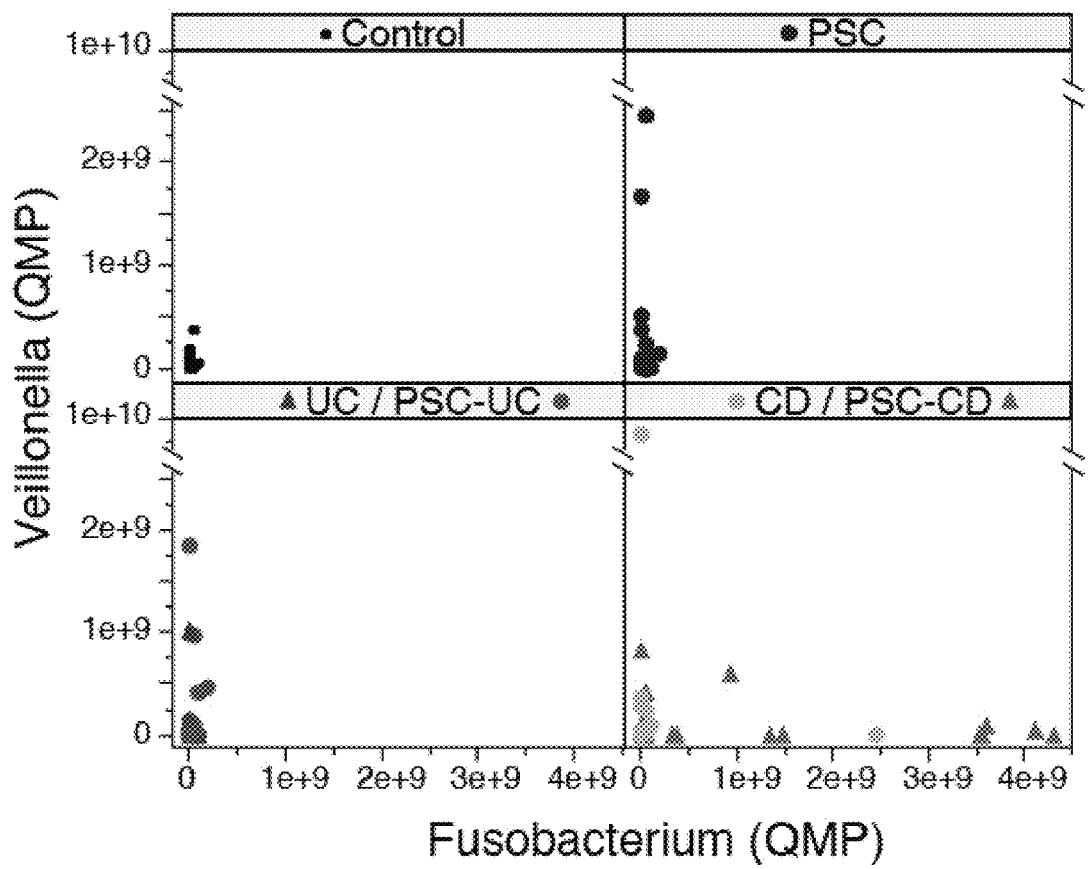

Revisiting the signature of PSC with QMP, we find several genera associated to PSC compared to healthy controls. *Fusobacterium* and *Veillonella* are positively associated while *Butyricimonas* and *Romboutsia* are negatively associated to intestinal inflammation beyond stool moisture variation (Nested linear model log-transformed, N=133, p-value<0.05; FIG. 8*a*). Several studies have explored the causal role of *Veillonella* and especially *Fusobacterium* species in potentiating a proinflammatory environment (Shreiner et al 2016 Curr Opin Gastroenterol 31:69-75; van den Bogert et al 2014 PLoS One 9:e114277), and these two have been reported to coexist for increased oxidative stress resistance in oral biofilms (Zhou et al 2017 Appl Environ Microbiol doi: 10.1128/AEM.01079-17). Here, we observe a striking coexclusion between Fusobacterium and *Veillonella* in faecal samples from the PSC/IBD cohort (Spearman, N=85 (samples missing both taxa excluded), rho=−0.346, p-value=0.0012) and while high-*Veillonella* individuals were found throughout the whole cohort, high-Fusobacterium were only found in CD and PSC-CD samples (FIG. 8*b*), suggesting competitive exclusion in the inflamed colon. Among those correlations no longer significant in the quantitative context, we highlight the positive association between Enterococcus and calprotectin measurements. Previously, we identified Enterococcus, Fusobacterium, and Lactobacillus as proportional marker genera of PSC, with elevated relative abundances in both PSC and PSC-IBD patients. Here, QMP analyses enabled us to disentangle the interwoven biliary obstruction and intestinal inflammation signals. While Fusobacterium was among the genera that positively correlated with calprotectin concentrations, Enterococcus remained the only PSC microbiome marker associated with serum alkanine phospathase (ALP) levels, a marker for bile duct obstruction severity (Spearman, N=89, rho=0.27, FDR=0.03), still significant even beyond after deconfounding for faecal moisture content (Nested linear model log-transformed, N=87, p-value=0.001). Of note, Enterococcus spp. have also been reported as the most common of isolates detected in bile samples of PSC patients (Pohl et al 2006 Eur J Gastroenterol Hepatol 18:69-74). No significant QMP associations between Lactobacillus and calprotectin/ALP concentrations were detected.

Example 4. Bacteroides2 Enterotype as Marker for MS

Figure 7:
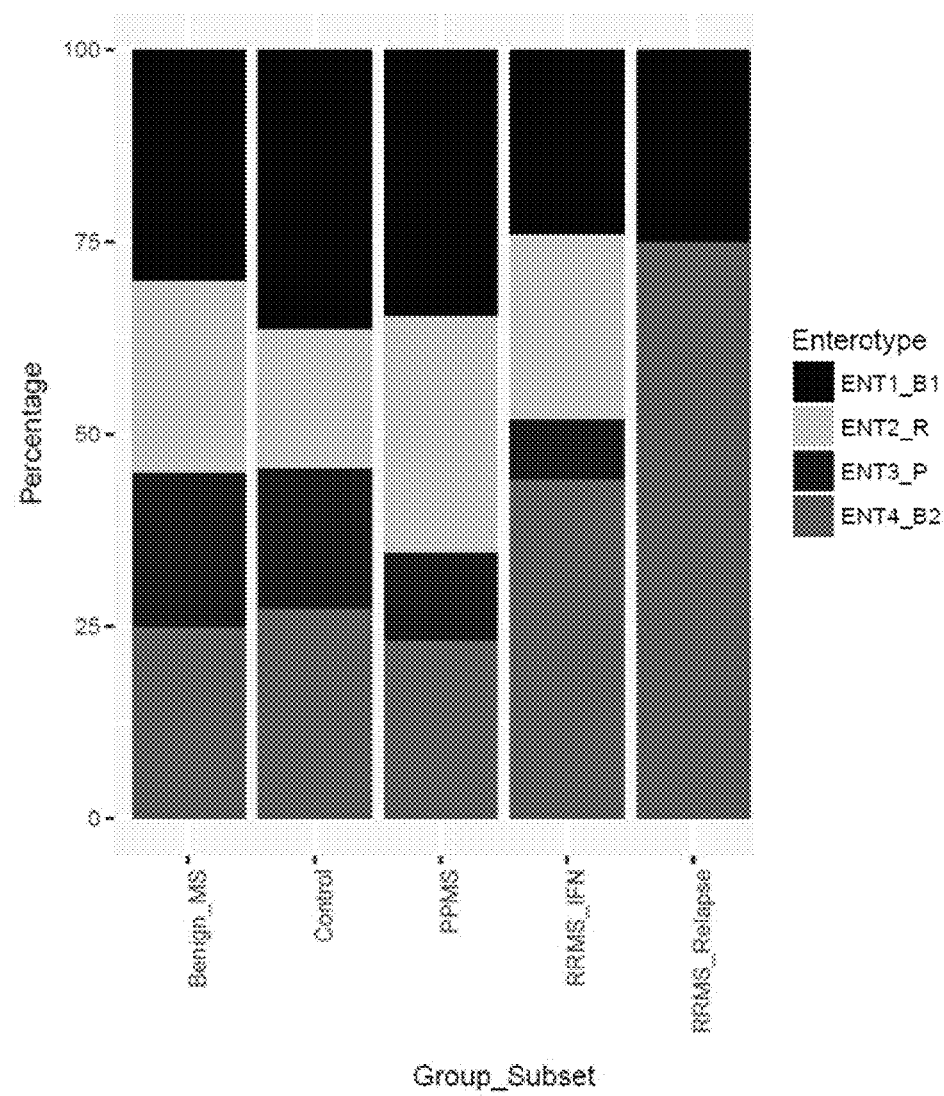
FIG. 7. Percentage of individuals with a specific enterotype per diagnose (group subset) (N=172). Bars represent from top to bottom: *Bacteroides* 1 (black); *Ruminococcaceae* (grey); *Prevotella* (blue) and *Bacteroides* 2 (purple). In the RRMS_relapse subset both *Ruminococcaceae* and *Prevotella* are missing. MS, multiple sclerosis; RR, relapsing-remitting; PP, primary progressive.

Multiple sclerosis (MS) is a chronic inflammatory and neurodegenerative disease characterized by substantial clinical heterogeneity. Most MS patients present with recurrent periods of relapses and remissions, with relapses thought to be provoked by the infiltration of adaptive immune cells into the central nervous system (CNS), hereby resulting in focal inflammation and myelin loss. Based on our findings that *Bacteroides*2 enterotype is associated with IBD and PSC, we questioned whether variations in the gut microbiota might explain differences in inflammatory disease activity and drive clinical heterogeneity in MS. We conducted a pilot study in a cohort of MS patients (N=118) with well-defined disease characteristics to assess differential diversity, genera abundance and enterotypes (*Bacteroides*1, *Bacteroides*2, *Prevotella* and *Ruminococcus*) among the different MS phenotypes (benign MS, PPMS, RRMS-relapse) and healthy controls (N=30), after correcting for stool consistency and other covariates. Additionally, we included an interferon treated RRMS group (RRMS_IFN). Interestingly, in both the interferon treated RRMS group and RRMS_relapse group a significantly increased percentage of the *Bacteroides* 2 enterotype is observed (FIG. 7).

MATERIALS AND METHODS

Sampling

Fecal samples from our previous study (Sabino et al 2016 Gut 65:1681-1689) were reanalysed. In short, these fecal samples were collected from patients with PSC, patients with CD and patients with ulcerative colitis (UC) attending the inflammatory bowel disease (IBD) or hepatology outpatient clinic of the University Hospitals of Leuven. The diagnosis of PSC and IBD was based on established guidelines (symptoms, endoscopy, imaging or histology). Age, gender and BMI matched healthy controls were selected from the Flemish Gut Flora Project (FGFP) (Falony et al 2016 Science 352:560-564). All patients and healthy controls signed informed consent before sample collection. The local ethical committee approved the study.

Concerning the MS study, MS patients, diagnosed according to the 2010 revised McDonald criteria (Polman et al 2011 Ann Neurol 69:292-302), were recruited from the National MS center Melsbroek and University Hospital Brussels, Belgium. Inclusion was based on the clinical phenotype and well-defined disease characteristics, considering presentation at onset, Expanded Disability Status Scale (EDSS), disease activity and treatment status. The RRMS group consisted of untreated active RRMS, untreated active RRMS during relapse and interferon (IFN) treated RRMS. Disease duration and EDSS were taken into account to define a subset of untreated BMS patients (Calabrese et al 2009 Mult Scler 15:36-41; Amato et al 2006 J Neurol 253:1054-1059). In the PPMS group, no relapses occurred within 2 years prior to screening. During enrolment, healthy controls were recruited, matched for age and gender against the whole MS study population. Written informed consent was obtained from patients and controls and the study was approved by the leading ethics committee.

Flow Cytometry

Cell counting procedure was performed on frozen (−80° C.) fecal aliquots using an Accuri BD flow cytometer as described in Vandeputte et al (2017 Nature) to obtain cell densities per gram of fecal material. Briefly, fecal aliquots were diluted 100,000 times in autoclaved physiological solution (8.5 g NaCl/l) and filtered using a sterile syringe filter (pore size of 5 µm). The sample was stained with 1 µL SYBR Green I (1:100 dilution in DMSO; shaded 15 min incubation at 37° C.; 10,000 concentrate, Thermo Fisher Scientific, Waltham, USA Thermo Fischer). Flow cytometric measurements were done using FL1 and FL3 channels for primary gating of the microbial population. Afterwards, FSC and SSC channels were used to gate out background events that were still present to determine accurate cell counts. The cell counts were converted to microbial loads per gram of fecal material (fresh weight).

Microbiota Phylogenetic Profiling

DNA extraction and sequencing data pre-processing. Fecal DNA extraction and microbiota profiling was performed as described previously (Sabino et al 2016 Gut 65:1681-1689). Briefly, DNA was extracted from fecal material using the MoBio PowerMicrobiome RNA isolation kit. The V4 region of the 16S rRNA gene was amplified with primer pair 515F/806R as described by Kozich et al. (2013 Appl Environ Microbiol 79:5112-5120). Sequencing was performed on the Illumina MiSeq platform (San Diego, Calif., USA), to generate paired-end reads of 250 bases in length in each direction. After de-multiplexing, fastq sequences were merged using FLASH (Magoc et al 2011 Bioinformatics 27:2957-2963) software with default parameters. Successfully combined reads were filtered based on quality (>90% of nucleotides with quality score of 30 or higher for every read) using Fastx tool kit (http://hannonlab.cshl.edu/fastx_toolkit/). Chimeras were removed with UCHIME (Magoc et al 2011 Bioinformatics 27:2957-2963; Edgar et al 2011 Bioinformatics 27:2194-2200).

Relative Microbiome Profiles (RMP)

For relative microbiome analyses, each sample was downsized to 10,000 reads by random selection of reads. The taxonomy of reads was assigned using RDP classifier 2.12 (Wang et al 2007 Appl Environ Microbiol 73:5261-5267).

Quantitative Microbiome Profiles (QMP)

The microbial flow cytometric measurements were used to transform sequencing data into an absolute genus abundance matrix. This methodology has three essential steps. Firstly, the reads that are classified at genus level are corrected for copy number variation, using RDP classifier 2.12 (Wang et al 2007 Appl Environ Microbiol 73:5261-5267). Secondly, samples were downsized to even sampling depth, defined as the ratio between sample size (16S rRNA gene copy number corrected sequencing depth) and microbial load (total cell counts per gram of fecal material (fresh weight)). Each sample was rarefied to the number of reads equivalent to the minimum observed sampling depth in the cohort that allowed to preserve at least 150 reads per sample. From the total 160 samples, only 27 samples are below 500 reads per sample. Hereby, some samples were excluded from the analysis. Thirdly, the obtained genus abundances within samples are made proportional and are then multiplied by the total microbial load per sample.

Fecal Calprotectin

Fecal calprotectin was measured with fCAL ELISA kit (Buhlmann, Schonenbuch, Switzerland), both in fresh and in frozen samples. Patients with PSC and patients with CD were asked to provide fresh fecal samples, which were frozen at −80° C. within 12 hours after sampling. Fecal calprotectin was measured in fresh aliquots from these samples. Samples from patients with UC were already available in our biobank, therefore, fecal calprotectin was measured in frozen aliquots from these samples. The FGFP volunteers were asked to provide a frozen fecal sample. Frozen aliquots from the FGFP samples were used for fecal calprotectin measurements. Some fresh fecal samples from patients were measured with Quantum Blue Calprotectin High Range (Buhlmann, Schonenbuch, Switzerland). The lower limit of detection of this test is 100 µg/g. Therefore, all samples measured with fCAL ELISA kit with fecal calprotectin values lower than 100 µg/g were set at 100 µg/g for statistical analysis. These samples will be measured again with fCAL ELISA kit.

Genotyping

All patients were already genotyped with Immunochip (Illumina, San Diego, Calif., USA) as part of past genome-wide association studies (Jostins et al 2012 Nature 491:119-24; Liu et al 2013 Nat Genet 45:670-675. A genetic risk score (GRS) was calculated for each patient with R package Mangrove (version 1.21) (Jostins et al 2013 PLoS One 8:e76328), taking into account the risk allele frequency and odds ratio of each single nucleotide polymorphism (SNP). The PSC GRS was calculated using the 16 risk SNPs for PSC and the IBD GRS was calculated using the 225 risk SNPs for IBD.

Statistical Analysis

R software (version 3.4.1) was used for statistical analysis. Parametric and non-parametric tests were used when applicable. Shapiro-Wilk test was used to test for normality. Numerical ecology statistics were facilitated by the phyloseq (version 1.20.0) and vegan (version 2.4-3) R packages. Mann-Whitney U was used to test median differences of genera abundances between different groups. Non-parametric Kruskal-Wallis test with post-hoc analysis with Dunn test were used to test differences between more than two groups. Parametric ANOVA with post-hoc Tukey test were used when ANOVA assumptions were met. Spearman correlation was used for correlations between two continuous variables. Comparison between two or more categorical variables was performed with Pearson's Chisquared test, followed by post-hoc pairwise Fisher tests when appropriate. All p-values were corrected for multiple testing when appropriate, the method (FDR or Bonferroni) used is always reported alongside the p values.

The invention claimed is:

1. A method of treating an inflammatory disorder in a subject in need thereof, the method comprising:
    quantifying the number of microbial cells in a stool sample from a patient;
    determining the relative fraction of the *Bacteroides* and *Faecalibacterium* genus in the stool sample;
    identifying the subject in need thereof after determining that the stool sample is characterized by:
        low microbial cell count as compared to a mean microbial cell count from a healthy subject population,
        an at least 10% higher relative fraction of the *Bacteroides* genus as compared to a mean relative fraction of the *Bacteroides* genus from the healthy subject population, and
        an at least 10% lower relative fraction of the *Faecalibacterium* genus as compared to a mean relative fraction of the *Faecalibacterium* genus from the healthy subject population; and
    administering an effective amount of anti-inflammatory medication to the subject.

2. The method according to claim 1, wherein the low microbial cell count is a cell count of less than $1.5 \times 10^{11}$ microbial cells per gram of stool.

3. The method according to claim 1, wherein the high relative fraction of the *Bacteroides* genus is the *Bacteroides* genus being among the 25% most abundant genera in the stool sample, and wherein the low relative fraction of the *Faecalibacterium* genus is the *Faecalibacterium* genus being among the 25% least abundant genera in the stool sample.

4. The method according to claim 1, wherein the step of determining that the stool sample is characterized by an at least 10% higher relative fraction of the *Bacteroides* genus and an at least 10% lower relative fraction of the *Faecalibacterium* genus, is determined by microbiota phylogenetic profiling.

5. The method according to claim 4, wherein the phylogenetic profiling is performed using polymerase chain reaction (PCR), reverse transcriptase PCR, quantitative PCR, multiplex PCR, high-throughput sequencing, metatranscriptomic sequencing, identification of strain-specific markers, or 16S rRNA analysis.

6. The method according to claim 1, wherein the stool sample is further characterized by lower bacterial diversity as compared to a stool sample from a healthy subject.

* * * * *

UNITED STATES PATENT AND TRADEMARK OFFICE
CERTIFICATE OF CORRECTION

| | | |
|---|---|---|
| PATENT NO. | : 11,649,508 B2 | Page 1 of 1 |
| APPLICATION NO. | : 16/771856 | |
| DATED | : May 16, 2023 | |
| INVENTOR(S) | : Jeroen Raes et al. | |

It is certified that error appears in the above-identified patent and that said Letters Patent is hereby corrected as shown below:

On the Title Page

In Column 1, Item (73) please replace "KATHOLIEKE UNIVERSITES" with --KATHOLIEKE UNIVERSITEIT--

In Column 1, Item (73) please replace "VRIJE UNIVERSITES" with --VRIJE UNIVERSITEIT--

Signed and Sealed this
Twenty-seventh Day of August, 2024

Katherine Kelly Vidal
*Director of the United States Patent and Trademark Office*